(12) United States Patent
Kopelman et al.

(10) Patent No.: US 12,171,575 B2
(45) Date of Patent: Dec. 24, 2024

(54) INTRAORAL SYSTEMS AND METHODS FOR SAMPLING SOFT-TISSUE

(71) Applicant: Align Technology, Inc., San Jose, CA (US)

(72) Inventors: Avi Kopelman, Palo Alto, CA (US); Srinivas Kaza, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 202 days.

(21) Appl. No.: 16/152,281

(22) Filed: Oct. 4, 2018

(65) Prior Publication Data

US 2019/0099129 A1 Apr. 4, 2019

Related U.S. Application Data

(60) Provisional application No. 62/568,212, filed on Oct. 4, 2017.

(51) Int. Cl.
*A61B 5/00* (2006.01)
*A61B 5/145* (2006.01)
(Continued)

(52) U.S. Cl.
CPC ............ *A61B 5/682* (2013.01); *A61B 5/0088* (2013.01); *A61B 5/14503* (2013.01);
(Continued)

(58) Field of Classification Search
CPC ... A61B 5/0088; A61B 5/14514; A61B 5/685; A61B 5/4552; A61B 5/682;
(Continued)

(56) References Cited

U.S. PATENT DOCUMENTS 2,171,695 A 9/1939 Harper
2,194,790 A 3/1940 Gluck
(Continued)

FOREIGN PATENT DOCUMENTS

AU 517102 B 11/1977
AU 3031677 A 11/1977
(Continued)

OTHER PUBLICATIONS

US 8,553,966 B1, 10/2013, Alpern et al. (withdrawn)
(Continued)

*Primary Examiner* — Sana Sahand
(74) *Attorney, Agent, or Firm* — Shay Glenn LLP

(57) ABSTRACT

Intraoral systems and methods including aligners having soft tissue sensors. The soft tissue sensors may detect protein biomarkers to determine effectiveness of the aligners for causing tooth movement according to a treatment plan. One or more microneedles may be configured to pass the protein biomarker to the soft tissue sensor. A processor may be configured to compare a detected level of the protein biomarker to an expected lever of the protein biomarker, and determine whether an aligner should be replaced. A bias may be configured to apply continuous force to hold the microneedle(s) against a patient's soft tissue. A controller may be configured to apply a biasing force to move the microneedles(s) from a retracted position to an extended position to penetrate the patient's soft tissue.

36 Claims, 13 Drawing Sheets

(51) Int. Cl.
*A61C 7/08* (2006.01)
*A61C 19/04* (2006.01)

(52) U.S. Cl.
CPC ........ *A61B 5/14514* (2013.01); *A61B 5/4552* (2013.01); *A61B 5/685* (2013.01); *A61B 5/6867* (2013.01); *A61B 5/14507* (2013.01); *A61B 5/4845* (2013.01); *A61B 5/688* (2013.01); *A61B 2562/046* (2013.01); *A61B 2562/066* (2013.01); *A61C 7/08* (2013.01); *A61C 19/04* (2013.01)

(58) Field of Classification Search
CPC ..... A61B 5/14539; A61B 5/01; A61B 5/0833; A61B 5/0836; A61B 5/038; A61B 5/4547; A61B 5/0002; A61B 10/0051; A61B 2562/028
See application file for complete search history.

(56) References Cited

U.S. PATENT DOCUMENTS

| | | |
|---|---|---|
| 2,467,432 A | 4/1949 | Kesling |
| 2,531,222 A | 11/1950 | Kesling |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |

(56) References Cited

U.S. PATENT DOCUMENTS

| | | |
|---|---|---|
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,615,183 A | 3/1997 | Ishii |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,199 A | 10/1998 | Khizh et al. |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,234,990 B1 * | 5/2001 | Rowe ................. A61B 5/14514 604/22 |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |

(56) References Cited

U.S. PATENT DOCUMENTS

| | | |
|---|---|---|
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |

(56) References Cited

U.S. PATENT DOCUMENTS

| | | |
|---|---|---|
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |

(56) References Cited

U.S. PATENT DOCUMENTS

| | | |
|---|---|---|
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,730,769 B2 | 8/2017 | Chen et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0113317 A1 | 5/2005 | Robinson et al. |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |

(56) References Cited

U.S. PATENT DOCUMENTS

| | | |
|---|---|---|
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1* | 5/2007 | Beiski .............. A61B 10/0051 600/349 |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0086890 A1 | 4/2010 | Kuo |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0028210 A1 | 2/2012 | Hegyi et al. |

(56) References Cited

U.S. PATENT DOCUMENTS

| | | |
|---|---|---|
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0109932 A1* | 5/2013 | Saadat ............... A61B 5/0873 600/383 |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Iowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338626 A1 | 11/2016 | Wang et al. |
| 2016/0338799 A1 | 11/2016 | Wu et al. |
| 2016/0346063 A1 | 12/2016 | Schulhof et al. |
| 2016/0367188 A1 | 12/2016 | Malik et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1* | 3/2017 | Alauddin ............... A61C 19/04 |
| 2017/0071705 A1 | 3/2017 | Kuo |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0115236 A1* | 4/2017 | Renlund .......... A61B 5/150984 |
| 2017/0122846 A1* | 5/2017 | Holmes .................... G01N 1/38 |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0252140 A1 | 9/2017 | Murphy et al. |
| 2017/0258555 A1 | 9/2017 | Kopelman |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2017/0347956 A1 | 12/2017 | Zegarelli |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0078334 A1* | 3/2018 | Lotan ...................... A61B 1/24 |

(56) References Cited

U.S. PATENT DOCUMENTS

| | | | |
|---|---|---|---|
| 2018/0085059 A1* | 3/2018 | Lee | A61B 5/4557 |
| 2018/0096465 A1 | 4/2018 | Levin | |
| 2018/0125610 A1 | 5/2018 | Carrier et al. | |
| 2018/0153648 A1 | 6/2018 | Shanjani et al. | |
| 2018/0153649 A1 | 6/2018 | Wu et al. | |
| 2018/0153733 A1 | 6/2018 | Kuo | |
| 2018/0168788 A1 | 6/2018 | Fernie | |
| 2018/0192877 A1 | 7/2018 | Atiya et al. | |
| 2018/0228359 A1 | 8/2018 | Meyer et al. | |
| 2018/0280118 A1 | 10/2018 | Cramer | |
| 2018/0284727 A1 | 10/2018 | Cramer et al. | |
| 2018/0318043 A1 | 11/2018 | Li et al. | |
| 2018/0368944 A1 | 12/2018 | Sato et al. | |
| 2018/0368961 A1* | 12/2018 | Shanjani | A61B 5/4547 |
| 2019/0026599 A1 | 1/2019 | Salah et al. | |
| 2019/0046296 A1 | 2/2019 | Kopelman et al. | |
| 2019/0046297 A1 | 2/2019 | Kopelman et al. | |
| 2019/0069975 A1 | 3/2019 | Cam et al. | |
| 2019/0076216 A1 | 3/2019 | Moss et al. | |
| 2019/0090983 A1 | 3/2019 | Webber et al. | |
| 2020/0214817 A1 | 7/2020 | Shanjani et al. | |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | 2016142414 A1 | 9/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |

(56) References Cited

FOREIGN PATENT DOCUMENTS

| WO | WO2018/232113 A1 | 12/2018 |
| WO | WO2019/018784 A1 | 1/2019 |

OTHER PUBLICATIONS beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Berland; The use of smile libraries for cosmetic dentistry; Dental Tribunne: Asia pacfic Edition; pp. 16-18; Mar. 29, 2006.
Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.
Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); retieved from te internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd Vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.
AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance; Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; (product

(56) References Cited

OTHER PUBLICATIONS information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.

Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/` pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ` A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.

(56) References Cited

OTHER PUBLICATIONS

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-x; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Muzio et al.; Minimum intensity projection (MinIP); 6 pages; retrieved from the internet (https://radiopaedia.org/articles/minimum-intensity-projection-minip) on Sep. 6, 2018.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Friede et al.; Accuracy of Cephalometric Prediction in Orthognathic Surgery; Journal of Oral and Maxillofacial Surgery; 45(9); pp. 754-760; Sep. 1987.
Friedrich et al; Measuring system for in vivo recording of force systems in orthodontic treatment-concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982 &Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel; Marker-Free Human Motion Capture in Dynamic Cluttered Environments from a Single View-Point, PhD Thesis; 171 pages; Dec. 2007.
Guess et al.; Computer Treatment Estimates in Orthodontics and Orthognathic Surgery; Journal of Clinical Orthodontics; 23(4); pp. 262-268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (Ansys Inc.'s finite element analysis software); 2 pages; retrieved from the Internet (http://static.highbeam.eom/t/toolingampproduction/november011996/simulatingstressputonfa..); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
Invisalign; You were made to move. There's never been a better time to straighten your teeth with the most advanced clear aligner in the world; Product webpage; 2 pages; retrieved from the internet (www.invisalign.com/) on Dec. 28, 2017.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

(56) References Cited

OTHER PUBLICATIONS

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kumar et al.; Rapid maxillary expansion: A unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

Mccann; Inside the ADA; J. Amer. Dent. Assoc, 118:286-294; Mar. 1989.

Mcnamara et al.; Invisible Retainers; J. Clin Orthod.; pp. 570-578; 11 pages; (Author Manuscript); Aug. 1985.

Mcnamara et al.; Orthodontic and Orthopedic Treatment in the Mixed Dentition; Needham Press; pp. 347-353; Jan. 1993.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy as One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; Cerec CAD/CAM Inlays: Aesthetics and Durability in a Single Appointment; Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.

Pinkham; Foolish Concept Propels Technology; Dentist, 3 pages , Jan./Feb. 1989.

Pinkham; Inventor's CAD/CAM May Transform Dentistry; Dentist; pp. 1 and 35, Sep. 1990.

Ponitz; Invisible retainers; Am. J. Orthod.; 59(3); pp. 266-272; Mar. 1971.

Procera Research Projects; Procera Research Projects 1993 ` Abstract Collection; 23 pages; (year of pub. sufficiently earlier than effective US filing date and any foreign priority date) 1993.

Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.

Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.

Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.

Redmond et al.; Clinical Implications of Digital Orthodontics; American Journal of Orthodontics and Dentofacial Orthopedics; 117(2); pp. 240-242; Feb. 2000.

Rekow et al.; CAD/CAM for Dental Restorations—Some of the Curious Challenges; IEEE Transactions on Biomedical Engineering; 38(4); pp. 314-318; Apr. 1991.

Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.

Rekow; A Review of the Developments in Dental CAD/CAM Systems; Current Opinion in Dentistry; 2; pp. 25-33; Jun. 1992.

Rekow; CAD/CAM in Dentistry: A Historical Perspective and View of the Future; Journal Canadian Dental Association; 58(4); pp. 283, 287-288; Apr. 1992.

Rekow; Computer-Aided Design and Manufacturing in Dentistry: A Review of the State of the Art; Journal of Prosthetic Dentistry; 58(4); pp. 512-516; Dec. 1987.

Rekow; Dental CAD-CAM Systems: What is the State of the Art?; The Journal of the American Dental Association; 122(12); pp. 43-48; Dec. 1991.

Rekow; Feasibility of an Automated System for Production of Dental Restorations, Ph.D. Thesis; Univ. of Minnesota, 250 pages, Nov. 1988.

Richmond et al.; The Development of the PAR Index (Peer Assessment Rating): Reliability and Validity.; The European Journal of Orthodontics; 14(2); pp. 125-139; Apr. 1992.

Richmond et al.; The Development of a 3D Cast Analysis System; British Journal of Orthodontics; 13(1); pp. 53-54; Jan. 1986.

Richmond; Recording the Dental Cast in Three Dimensions; American Journal of Orthodontics and Dentofacial Orthopedics; 92(3); pp. 199-206; Sep. 1987.

Rudge; Dental Arch Analysis: Arch Form, A Review of the Literature; The European Journal of Orthodontics; 3(4); pp. 279-284; Jan. 1981.

Sahm et al.; "Micro-Electronic Monitoring of Functional Appliance Wear"; Eur J Orthod.; 12(3); pp. 297-301; Aug. 1990.

(56) References Cited

OTHER PUBLICATIONS

Sahm; Presentation of a wear timer for the clarification of scientific questions in orthodontic orthopedics; Fortschritte der Kieferorthopadie; 51 (4); pp. 243-247; (Translation Included) Jul. 1990.

Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Schellhas et al.; Three-Dimensional Computed Tomography in Maxillofacial Surgical Planning; Archives of Otolaryngology—Head and Neck Surgery; 114(4); pp. 438-442; Apr. 1988.

Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.

Shilliday; Minimizing finishing problems with the mini-positioner; American Journal of Orthodontics; 59(6); pp. 596-599; Jun. 1971.

Shimada et al.; Application of optical coherence tomography (OCT) for diagnosis of caries, cracks, and defects of restorations; Current Oral Health Reports; 2(2); pp. 73-80; Jun. 2015.

Siemens; Cerec—Computer-Reconstruction, High Tech in der Zahnmedizin; 15 pagesl; (Includes Machine Translation); (year of pub. sufficiently earlier than effective US filing date and any foreign priority date); 2004.

Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.

Sirona Dental Systems GmbH, Cerec 3D, Manuel utiiisateur, Version 2.0X (in French); 114 pages; (English translation of table of contents included); (year of pub. sufficiently earlier than effective US filing date and any foreign priority date); 2003.

Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

Sturman; Interactive Keyframe Animation of 3-D Articulated Models; Proceedings Graphics Interface '84; vol. 86; pp. 35-40; May-Jun. 1984.

The American Heritage, Stedman's Medical Dictionary; Gingiva; 3 pages; retrieved from the interent (http://reference.com/search/search?q=gingiva) on Nov. 5, 2004.

The Dental Company Sirona: Cerc omnicam and cerec bluecam brochure: The first choice in every case; 8 pages; (year of pub. sufficiently earlier than effective US filing date and any foreign priority date) 2014.

Thera Mon; "Microsensor"; 2 pages; retrieved from the internet (www.english.thera-mon.com/the-product/transponder/index.html); on Sep. 19, 2016.

Thorlabs; Pellin broca prisms; 1 page; retrieved from the internet (www.thorlabs.com); Nov. 30, 2012.

Tiziani et al.; Confocal principle for macro and microscopic surface and defect analysis; Optical Engineering; 39(1); pp. 32-39; Jan. 1, 2000.

Truax; Truax Clasp-Less(TM) Appliance System; The Functional Orthodontist; 9(5); pp. 22-24, 26-8; Sep.-Oct. 1992.

Tru-Tatn Orthodontic & Dental Supplies, Product Brochure, Rochester, Minnesota 55902, 16 pages; (year of pub. sufficiently earlier than effective US filing date and any foreign priority date) 1996.

U.S. Department of Commerce, National Technical Information Service, Holodontography: An Introduction to Dental Laser Holography; School of Aerospace Medicine Brooks AFB Tex; Mar. 1973, 40 pages; Mar. 1973.

U.S. Department of Commerce, National Technical Information Service; Automated Crown Replication Using Solid Photography SM; Solid Photography Inc., Melville NY,; 20 pages; Oct. 1977.

Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.

Van Der Linden et al.; Three-Dimensional Analysis of Dental Casts by Means of the Optocom; Journal of Dental Research; 51(4); p. 1100; Jul.-Aug. 1972.

Van Der Linden; A New Method to Determine Tooth Positions and Dental Arch Dimensions; Journal of Dental Research; 51(4); p. 1104; Jul.-Aug. 1972.

Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.

Van Hilsen et al.; Comparing potential early caries assessment methods for teledentistry; BMC Oral Health; 13(16); doi: 10.1186/1472-6831-13-16; 9 pages; Mar. 2013.

Varady et al.; Reverse Engineering of Geometric Models`An Introduction; Computer-Aided Design; 29(4); pp. 255-268; 20 pages; (Author Manuscript); Apr. 1997.

Verstreken et al.; An Image-Guided Planning System for Endosseous Oral Implants; IEEE Transactions on Medical Imaging; 17(5); pp. 842-852; Oct. 1998.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23(10); pp. 694-700; Oct. 1989.

Watson et al.; Pressures recorded at te denture base-mucosal surface interface in complete denture wearers; Journal of Oral Rehabilitation 14(6); pp. 575-589; Nov. 1987.

Wells; Application of the Positioner Appliance in Orthodontic Treatment; American Journal of Orthodontics; 58(4); pp. 351-366; Oct. 1970.

Wikipedia; Palatal expansion; 3 pages; retrieved from the internet (https://en.wikipedia.org/wiki/Palatal_expansion) on Mar. 5, 2018.

Williams; Dentistry and CAD/CAM: Another French Revolution; J. Dent. Practice Admin.; 4(1); pp. 2-5 Jan./Mar. 1987.

Williams; The Switzerland and Minnesota Developments in CAD/CAM; Journal of Dental Practice Administration; 4(2); pp. 50-55; Apr./Jun. 1987.

Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.

Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

Wolf; Three-dimensional structure determination of semi-transparent objects from holographic data; Optics Communications; 1(4); pp. 153-156; Sep. 1969.

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.

Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.

Yamada et al.; Simulation of fan-beam type optical computed-tomography imaging of strongly scattering and weakly absorbing media; Applied Optics; 32(25); pp. 4808-4814; Sep. 1, 1993.

Yamamoto et al.; Optical Measurement of Dental Cast Profile and Application to Analysis of Three-Dimensional Tooth Movement in

(56) References Cited

OTHER PUBLICATIONS

Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Grove et al.; U.S. Appl. No. 15/726,243 entitled "Interproximal reduction templates," filed Oct. 5, 2017**.
Riley et al.; U.S. Appl. No. 16/003,841 entitled Palatal expander with skeletal anchorage devices, filed Jun. 8, 2018**.
Shanjani et al.; U.S. Appl. No. 16/019,037 entitled "Biosensor performance indicator for intraoral appliances," filed Jun. 26, 2018**.
Sato et al.; U.S. Appl. No. 16/041,606 entitled "Palatal contour anchorage," filed Jul. 20, 2018**.
Xue et al.; U.S. Appl. No. 16/010,087 entitled "Automatic detection of tooth type and eruption status," filed Jun. 15, 2018**.
Sato et al.; U.S. Appl. No. 16/048,054 entitled "Optical coherence tomography for orthodontic aligners," filed Jul. 27, 2018**.
Miller et al.; U.S. Appl. No. 16/038,088 entitled "Method and apparatuses for interactive ordering of dental aligners," filed Jul. 17, 2018**.
Moalem et al.; U.S. Appl. No. 16/046,897 entitled Tooth shading, transparency and glazing, filed Jul. 26, 2018**.
Nyukhtikov et al.; U.S. Appl. No. 15/998,883 entitled "Buccal corridor assessment and computation," filed Aug. 15, 2018**.
Arakawa et al; Mouthguard biosensor with telemetry system for monitoring of saliva glucose: A novel cavitas sensor; Biosensors and Bioelectronics; 84; pp. 106-111; Oct. 2016.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
Dental Monitoring; Basics: How to put the cheek retractor?; 1 page (Screenshot); retrieved from the interenet (https://www.youtube.com/watch?v=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.
Ecligner Selfie; Change your smile; 1 page (screenshot); retrieved from the internet (https:play.google.com/store/apps/details?id=parklict.ecligner); on Feb. 13, 2018.
Martinelli et al.; Prediction of lower permanent canine and premolars width by correlation methods; The Angle Orthodontist; 75(5); pp. 805-808; Sep. 2005.
Nourallah et al.; New regression equations for prediciting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
Sobral De Agular et al.; The gingival crevicular fluid as a source of biomarkers to enhance efficiency of orthodontic and functional treatment of growing patients; Bio. Med. Research International; vol. 2017; pp. 1-7; Article ID 3257235; (year of pub. sufficiently earlier than effective US filing date and any foreign priority date) 2017.
Levin; U.S. Appl. No. 16/282,431 entitled "Estimating a surface texture of a tooth," filed Feb. 2, 2019.
Chen et al.; U.S. Appl. No. 16/223,019 entitled "Release agent receptacle," filed Dec. 17, 2018.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; Acs Sensors; 1(5); pp. 464-482; May 11, 2016.
Imani et al.; A wearable chemical-electrophysiological hybrid biosensing system for real-time health and fitness monitoring; Nature Communications; 7; 11650. doi 1038/ncomms11650; 7 pages; May 23, 2016.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Jeerapan et al.; Stretchable biofuel cells as wearable textile-based self-powered sensors; Journal of Materials Chemistry A; 4(47); pp. 18342-18353; Dec. 21, 2016.
Kim et al.; Advanced materials for printed wearable electrochemical devices: A review; Advanced Electronic Materials; 3(1); 15 pages; 1600260; Jan. 2017.
Kim et al.; Noninvasive alcohol monitoring using a wearable tatto-based iontophoretic-biosensing system; Acs Sensors; 1(8); pp. 1011-1019; Jul. 22, 2016.
Kim et al.; Non-invasive mouthguard biosensor for continuous salivary monitoring of metabolites; Analyst; 139(7); pp. 1632-1636; Apr. 7, 2014.
Kim et al.; A wearable fingernail chemical sensing platform: pH sensing at your fingertips; Talanta; 150; pp. 622-628; Apr. 2016.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.

(56) References Cited

OTHER PUBLICATIONS

Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Parrilla et al.; A textile-based stretchable multi-ion potentiometric sensor; Advanced Healthcare Materials; 5(9); pp. 996-1001; May 2016.
Windmiller et al.; Wearable electrochemical sensors and biosensors: a review; Electroanalysis; 25(1); pp. 29-46; Jan. 2013.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Elbaz et al.; U.S. Appl. No. 16/188,262 entitled "Intraoral scanner with dental diagnostics capabilities," filed Nov. 12, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.
D'Apuzzo et al., "Biomarkers of Periodontal Tissue Remodeling During Orthodontic Tooth Movement in Mice and Men: Overview and Clinical Relevance," The Scientific World Journal, Apr. 23, 2013, pp. 1-8.
Merriam-Webster., "Identify." 2022, pp. 3-6, Retrieved from the Internet: [URL: https://www.merriam-webster.com/dictionary/identify] [retrieved on Apr. 3, 2022].
Farooq et al.; Relationship between tooth dimensions and malocclusion; JPMA: The Journal of the Pakistan Medical Association; 64(6); pp. 670-674; Jun. 2014.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
ormco.com; Increasing clinical performance with 3D interactive treatment planning and patient-specific appliances; 8 pages; retrieved from the internet (http://www.konsident.com/wp-content/files_mf/1295385693http___ormco.com_index_cmsfilesystemaction_fileOrmcoPDF_whitepapers.pdf) on Feb. 27, 2019.
Video of DICOM to Surgical Guides; Can be viewed at <URL:https://youtu.be/47KtOmCEFQk; Published Apr. 4, 2016.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.

\* cited by examiner

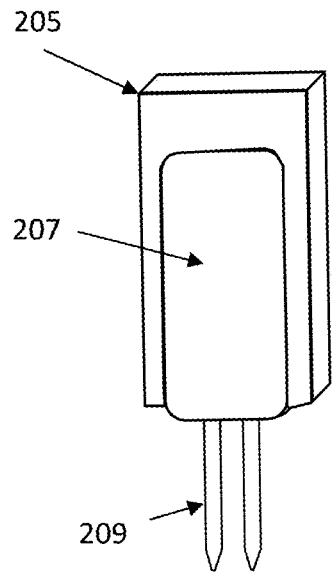 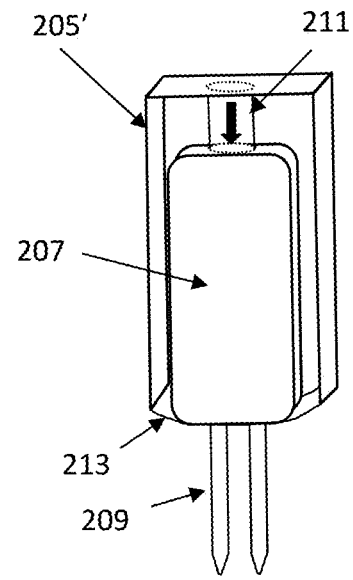
FIG. 2A          FIG. 2B
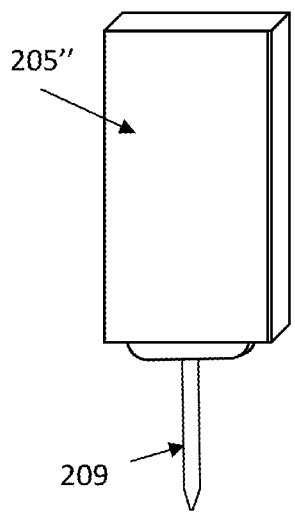 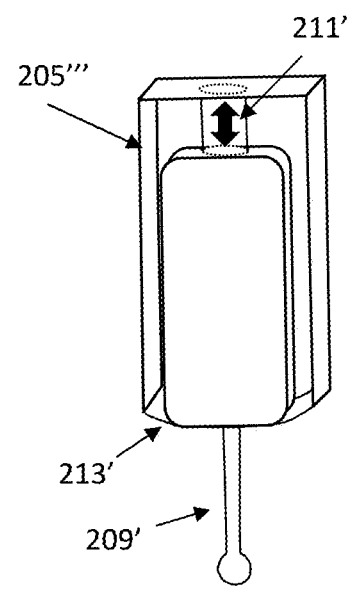
FIG. 2C          FIG. 2D

FIG. 3A  FIG. 3B

INTRAORAL SYSTEMS AND METHODS FOR SAMPLING SOFT-TISSUE

CROSS REFERENCE TO RELATED APPLICATIONS

This patent application claims priority to U.S. Provisional Patent Application No. 62/568,212, filed on Oct. 4, 2017 ("INTRAORAL APPLIANCES FOR SAMPLING SOFT-TISSUE"), which is herein incorporated by reference in its entirety.

This application may be related to U.S. patent application Ser. No. 16/019,037, filed on Jun. 26, 2018 ("BIOSENSOR PERFORMANCE INDICATOR FOR INTRAORAL APPLIANCES"), which claimed priority to U.S. provisional patent No. 62/525,082, filed Jun. 26, 2017 ("BIOSENSOR PERFORMANCE INDICATOR FOR INTRAORAL APPLIANCES"), each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are gingival sensors for sensing one or more analytes from the gingiva while being stably held in position against the teeth.

BACKGROUND

Blood and oral fluids that are obtained from the tissues surrounding the teeth may be used for diagnostic or therapeutic purposes. Typically samples of blood or other fluids are extracted by an external sampler (such as a needle) and sampled and/or analyzed external systems that examine the fluid to identify analytes of interests. Such techniques may make it difficult to provide longer, longitudinal analyses or continuous monitoring.

Further, such methods are typically not suitable for infants, disabled patients, patient suffering from needles fear and patients that need frequent body fluids sampling, mass monitoring and ordinary patients asking to spare the inconvenience that may be involved.

SUMMARY OF THE DISCLOSURE

Described herein are apparatuses, including systems and devices, configured to secure one or more sensors against a soft tissue while remaining secured to a hard tissue. In particular, described herein are sensors and sensor holders that are configured to couple to a hard tissue, such as the teeth, for accessing a soft tissues, such as the gingiva. In general, these apparatuses, and methods of using them, may include an intraoral appliance, including but not limited to an aligner, that is configured to secure to a patient's teeth and hold one or more sensors, including in particular soft tissue sensors.

For example, described herein are devices including a hard tissue anchoring portion having a tooth-holding channel or region that is configured to fit over all or portion of a patient's dental arch, and a one or more sensors attached (removably or permanently attached) that extends from the hard tissue anchoring portion towards the soft tissue, such as the patient's gingiva. The sensor may include one or more microneedles for sampling from the soft tissue. For example, any of the apparatuses described herein may include a sensor having one or more microneedles for accessing to the patient's soft tissue.

The hard tissue anchoring portion generally removably attaches to the patient's teeth. The hard tissue anchoring portion may be configured as a dental appliance that can be applied and removed over the patient's teeth. The dental appliance may be an intraoral appliance that is configured to set securely onto the patient's dental arch. The dental appliance may be secured by friction fit, onto the teeth. The dental appliance may be secured to all, or substantially all, of the patient's teeth in the upper and/or lower jaw, or it may be secured to just a subset of the patient's teeth in the upper or lower jaw.

For example, described herein are intraoral, soft-tissue sensor systems that include: an intraoral appliance shaped to receive a patient's teeth within a cavity and to secure the intraoral appliance against the patient's teeth; a soft tissue sensor mounted to the intraoral appliance, wherein the soft tissue sensor comprises one or more microneedles projecting from the intraoral appliance that are configured to penetrate soft tissue adjacent to the patient's teeth when worn, wherein the soft tissue sensor is configured to detect at least one analyte through the one or more microneedles; and a bias coupled to the soft tissue sensor configured to apply a biasing force to the soft tissue sensor. The bias may be activated, so that the sensor and/or the microneedle is held further away from the gingiva when initially worn, and once the intraoral appliance is worn on the teeth, the bias may be triggered (activated) to extend the microneedle (which may generally include both tissue penetrating and non-penetrating microneedles) towards, against, and/or into the soft tissue such as the gingiva and/or palate.

The soft tissue sensor may be removably mounted to the intraoral appliance, or permanently mounted to the intraoral appliance. A soft tissue sensor may include a fluid sensor that is configured to sense a property (electrical, chemical, mechanical, etc.) from the soft tissue such as the gingiva, and/or saliva, interstitial fluid, lymph, or blood associated with the gingiva. For example, the soft tissue sensor may be a sensor that penetrates into the soft tissue, such as the gingiva, in order to detect and/or measure a property from within the tissue. Alternatively or additionally, the soft tissue sensor may be configured to sample a fluid from within the gingiva by penetrating the soft tissue (e.g., with one or more hollow or solid microneedles) and allow the fluid to make contact with the needle or an inner lumen of the needle. A soft tissue sensor may be an electrical sensor that is configured to contact the soft tissue (without penetrating or with penetrating) and measure one or more properties.

The soft tissue sensor may generally be positioned on the intraoral appliance so as to not interfere with the patient's bite when worn. For example, the sensor may be held on an outer buccal or lingual side of the appliance, but may avoid the occlusal surface. The soft tissue sensor may also be shaped so that when engaged with the appliance, it does not protrude or provide any abrupt and/or rough surfaces. For example, one or more outward-facing surfaces or sides of the soft tissue sensor may be smooth and/or curved so that the tongue does not scrape against it.

The soft tissue sensor, and particularly any portion mounted or configured to be mounted on the buccal side of the intraoral appliance, may be configured so as to blend in with the appliance and/or the patient's teeth. For example, the soft tissue sensor may be formed of a translucent or transparent material. Alternatively, the soft tissue sensor may be colored to match the teeth and/or the intraoral appliance.

The soft tissue sensor may be configured to passively sense analyte or to actively sense analyte. For example, the soft tissue sensor include an optical sensor that illuminates a portion of the tissue with a specific wavelength and receives reflected and/or transmitted light passing through the soft tissue, blood, lymph, interstitial fluid, and/or saliva. The soft tissue sensor may be configured to extract material from the soft tissue (e.g., blood, saliva, interstitial fluid, lymph, etc.). The soft tissue sensor may comprise a chemical, immunohistochemical, enzymatic, or other sensor. Optical sensors may include near- and mid-IR sensors, florescence sensors (e.g., FRET), optical coherence tomography sensors, spectrographic sensors, etc. An optical sensor may be coupled with the microneedle and/or may sample material from the microneedle. An optical fiber may be held with or within the microneedle.

Any of the soft tissue sensors described herein may be configured to deliver material to the soft tissue, e.g., through the microneedle.

In general, the microneedle may be any appropriate needle, hollow or solid, that is 1 millimeter or less in diameter (e.g., 0.9 mm or less, 0.8 mm or less, 0.7 mm or less, 0.6 mm or less, 0.5 mm or less, 0.4 mm or less, 0.3 mm or less, 0.2 mm or less, 0.1 mm or less, etc.). The microneedle may extend from a base or substrate by any appropriate length (e.g., between 0.5 mm and 5 cm, e.g., between 0.5 cm and 4 cm, between 0.5 mm and 3 cm, between 0.5 mm and 1 cm, between 0.5 mm and 9 mm, between 0.5 mm and 8 mm, between 0.5 mm and 7 mm, between 0.5 mm and 6 mm, between 0.5 mm and 5 mm, etc.). The microneedle may be fabricated from any appropriate material, including metal, silicon (or silicon dioxide), polymer, etc., including combinations of these.

In general, any of the apparatuses described herein may include a bias (e.g., spring, elastic, etc.) that is configured to hold or drive the sensor or a sensing portion of the sensor (e.g., microneedle) against the soft tissue or to otherwise maintain contact and/or penetration with the soft tissue. In some variations the apparatus includes a spring bias. Any spring bias may be included (e.g., coil spring, flat spring, serpentine spring, leaf spring, v-spring, etc., gas spring, etc.). The bias may be configured to apply a force, and particularly a continuous force, on the soft tissue sensor to hold the sensor against the patient's soft tissue. The spring may be configured to limit the maximum amount of force applied (e.g., to less than 1 N, less than 0.5 N, less than 0.1 N, etc.). The bias may be part of the sensor (e.g., on an outer surface of the sensor) or part of the intraoral appliance holding the sensor.

Any of the intraoral appliances described herein may be configured to couple to the teeth, as mentioned above. In addition, the intraoral appliance may be configured to couple to the palate (soft and/or hard palate). For example, any of the intraoral appliances described herein may include a palatal region covering all or a portion of the palate. Further, any of these apparatuses may include one or more temporary anchorage devices.

Any of these intraoral appliances may be configured to mount to the hard tissue, including the teeth. For example, any of these apparatuses may include one or more attachment sites on the intraoral appliance configured to couple with the one or more temporary anchorage devices. Attachments may be affixed to the outside (e.g., buccal and/or lingual sides) of a tooth or teeth, e.g., by bonding. The attachment may couple to an attachment receiver on the intraoral appliance. Alternatively or additionally, the intraoral appliance may be configured to screw into a tooth, including onto a prosthetic tooth.

Any appropriate soft tissue sensor may be used, and may be configured to detect one or more analytes. For example, the soft tissue sensor may be configured to detect one or more of: electrolytes (e.g., fluoride, sodium, etc.), pH, glucose level, hydration, white blood cell count, lactate level, an inflammatory marker, a bacterial marker, air flow during inhaling and/or exhalation; chemical content of air inhaled; chemical content of air exhaled; bad breath, alcohol level.

The intraoral appliance provide a stable base or frame against which the sensor(s) may be held to the soft tissue, allowing sable sensing from the soft tissue. The intraoral appliance may also permit one or more sensors to be attached at more than one location, allowing rotation of the position of the sensor within the patient's mouth, preventing or reducing irritation. For example, the apparatuses described herein may allow a sensor to be attached to the intraoral appliance at a first position that allow sampling from a first region of the patient's mouth (anterior, etc.). The same sensor or a different sensor, including a different sensor of the same type (e.g., also including a microneedle) may then be moved, in the same intraoral appliance or another intraoral appliance, relative to the first positon, to a second position, allowing sampling of a separate region of the patient's mouth for a second time period (e.g., until removal of the intraoral appliance, such as one hour, 2 hours, 3 hours, 4 hours, 5 hours, 12 hours, 1 day, 2 days, 3 days, etc.).

Also described herein are methods of using any of the apparatuses described herein, including in particular, described herein are methods of monitoring (including methods of continuously monitoring) or detecting an analyte from a patient's soft tissue. For example, a method of detecting an analyte from a patient's soft tissue may include: placing an intraoral appliance onto the patient's teeth so that the patient's teeth are secured within a cavity of the intraoral appliance; biasing a soft tissue sensor mounted to the intraoral appliance against the soft tissue, wherein the soft tissue sensor comprises one or more microneedles projecting from the intraoral appliance, further wherein biasing comprises applying a biasing force to the soft tissue sensor to penetrate a soft tissue adjacent to the patient's teeth; and sensing an analyte through the one or more microneedles.

As mentioned, biasing may comprise applying a continuous force. The biasing force may be variable or constant. For example, biasing may comprise applying a continuous force from a spring. The method of sensing the analyte may comprise detecting one or more of: air flow during inhaling and/or exhalation; chemical content of air inhaled; chemical content of air exhaled; bad breath, alcohol level, glucose level, an inflammatory marker, or a bacterial marker.

Other apparatuses described herein may include intraoral, soft-tissue sensor systems in which the sensor (e.g., a sensor with one or more microneedles) may removably attached from the hard-tissue secured portion, e.g., an intraoral appliance. For example an intraoral soft-tissue sensing system may include: an intraoral appliance shaped to receive a patient's teeth within a cavity and to secure the intraoral appliance against the patient's teeth; and a soft tissue sensor detachably mounted to the intraoral appliance, wherein the soft tissue sensor comprises one or more microneedles projecting from the intraoral appliance that are configured to penetrate soft tissue adjacent to the patient's teeth when worn, wherein the soft tissue sensor is configured to detect at least one analyte from the patient's soft tissue through the one or more microneedles.

Any of these apparatuses may be configured to lock or otherwise secure the soft tissue sensor to the intraoral appliance. The intraoral appliance may include a snap, claps, strap, button, or any other fastener that may be used to secure the sensor in a fixed position in/on the intraoral appliance. The lock may be releasable or not releasable (e.g., single-use, etc.).

Any of the variations described above, may be incorporated into the apparatuses having a removable sensor.

Also described herein are intraoral, soft-tissue sensor systems that are configured to receive a sensor, but which do not include the sensor. For example, the sensor may be provided by a third party that uses the apparatus described herein to hold the sensor. For example, any of the apparatuses described herein may be configured to include a mount, which may have a standard or typical size, for receiving a sensor, so as to hold the sensor in stable position (relative to the hard tissue, e.g., teeth) for sensing from a soft tissue. The holder may be configured to releasably hold the sensor. For example, described herein are intraoral, soft-tissue systems (configured a stable sensor mounts) including: an intraoral appliance shaped to receive a patient's teeth within a cavity and to secure the intraoral appliance against the patient's teeth; and a soft tissue sensor mount on an outer surface of the intraoral appliance, wherein the soft tissue sensor mount is configured to detachably mount a soft tissue sensor to the intraoral appliance. Optionally, any of these apparatuses may include a soft tissue sensor configured to mount to the soft tissue sensor mount so that one or more microneedles project from the intraoral appliance to penetrate soft tissue adjacent to the patient's teeth when the intraoral appliance is worn by the patient. The soft tissue sensor may be configured to detect at least one analyte from the patient's soft tissue through the one or more microneedles.

For example, an intraoral, soft-tissue sensor system customized to fit a patient's dentition may include: a plurality of intraoral appliances, wherein each intraoral appliance is shaped to receive the patient's teeth within a cavity and to secure the intraoral appliance against the patient's teeth, further wherein each intraoral appliance is divided up into a plurality of regions; a soft tissue sensor mounted on each of the intraoral appliances, wherein the soft tissue sensor mounted on each of the intraoral appliances comprises one or more microneedles projecting from the intraoral appliance to which it is mounted, wherein the one or more microneedles are configured to penetrate soft tissue adjacent to the patient's teeth when worn to detect at least one analyte through the one or more microneedles; and wherein the soft tissue sensor mounted on each of the intraoral appliances is mounted to a different regions of each of the intraoral appliances compared to the other intraoral appliances in the plurality of intraoral appliances.

As mentioned above, any of the intraoral appliances in the plurality of intraoral appliances may include a bias coupled to the soft tissue sensor mounted on the intraoral appliance, wherein the bias is configured to apply a biasing force to the soft tissue sensor to secure the soft tissue sensor against and/or in the soft tissue when worn.

The different regions of the plurality of regions may be separated from each other by any appropriate distance. For example, the different regions of the plurality of regions may be separated from each other by a separation of greater than 0.5 mm (e.g., greater than about: 0.6 mm, 0.7 mm, 0.8 mm, 0.9 mm, 1 mm, 1.1 mm, 1.2 mm, 1.3 mm, 1.4 mm, 1.5 mm, 2 mm, etc.).

The plurality of intraoral appliances may be arranged in an ordered sequence such that, after the first intraoral appliance in the sequence, the region to which the soft tissue sensor is mounted in each subsequent intraoral appliance in the ordered sequence are not adjacent to the region to which the soft tissue sensor is mounted in the proceeding intraoral appliance in the ordered series.

In any of these intraoral appliances, the cavity may be configured to hold the patient's upper or lower arch. As mentioned above, each intraoral appliance of the plurality of intraoral appliances may include a palatal region configured to be positioned adjacent to the patient's palate when worn (either touching or not touching, e.g., separately by a distance of greater than about 0.1 mm, 0.2 mm, 0.3 mm, 0.4 mm 0.5 mm, 0.6 mm, 0.7 mm, 0.8 mm, 0.9 mm, 1 mm, etc.).

Any of the intraoral appliance described herein (including those of a series, e.g., plurality of intraoral appliances) may be configured to receive the patient's molar tooth or teeth, and/or the patient's incisor tooth or teeth, and/or the patient's canine tooth or teeth.

Also described herein are systems including a plurality of intraoral appliances in which each of the appliances includes a different sensor mount location. For example, an intraoral, soft-tissue sensor system customized to fit a patient's dentition may include: a plurality of intraoral appliances, wherein each intraoral appliance is shaped to receive the patient's teeth within a cavity and to secure the intraoral appliance against the patient's teeth, further wherein each intraoral appliance is divided up into a plurality of regions extending along the length of the intraoral appliance; a soft tissue sensor mount on an outer surface of each of the intraoral appliances of the plurality of intraoral appliances, wherein each soft tissue sensor mount is configured to detachably secure a soft tissue sensor to the intraoral appliance, further wherein the soft tissue sensor mounts on each of the intraoral appliances are located on different regions of each of the intraoral appliances compared to the locations of the soft tissue sensor mounts on each of the other intraoral appliances in the plurality of intraoral appliances.

For example, described herein are system wherein the soft tissue sensor mounts on each of the different intraoral appliance mounting locations and each intraoral appliances comprises a bias configured to couple to a soft tissue sensor and to apply a biasing force to the soft tissue sensor.

Any of these apparatuses (including these systems) may include a soft tissue sensor configured to mount to the soft tissue sensor mounts of each of the plurality of intraoral appliances so that one or more microneedles of the soft tissue sensor project to penetrate soft tissue adjacent to the patient's teeth when the intraoral appliance is worn by the patient, further wherein the soft tissue sensor is configured to detect at least one analyte from the patient's soft tissue through the one or more microneedles.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1A, the sensor is held in a sensor mount at a first location relative to the intraoral appliance, and multiple microneedles extend down from the sensor.

FIGS. 2A-2D illustrate examples of different variations of sensor mounts that may be included as part of an intraoral appliance of the apparatuses described herein. In FIG. 2A the sensor mount is shown with a sensor inside of the mount, surrounded on four (of six) sides of the mount (open on the face and bottom). In FIG. 2B, the sensor mount includes a bias driving the sensor held within the mount down (e.g., towards the gingival tissue). In FIG. 2C the sensor mount is enclosed on all but one side (e.g., the bottom) with the sensor secured within it. This variation may also include a bias. In this example, the sensor includes a single microneedle. FIG. 2D shows another example, similar to that shown in FIG. 2B in which the sensor mount includes a bias driving a single probe, configured as a non-penetrating probe, down onto the tissue.

FIGS. 3A-3C illustrate an example of a sensor mount on an intraoral appliance having a bias that can be activated (e.g., by manually pushing a button, upon wearing the intraoral appliance on the teeth, or by a remote signal, etc.) to extend, and in some cases retract, the sensor and/or the microneedles from the intraoral appliance. In FIG. 3A the sensor and microneedles are retracted. In FIG. 3B the bias has been activated driving the microneedles down, e.g., into the soft tissue. Optionally, the sensor and/or sensor mount may be configured so that the bias may be deactivated or retracted, withdrawing the needles, as shown in FIG. 3C.

DETAILED DESCRIPTION

Oral sensors, and particularly soft-tissue sensors, may be used as part of an apparatus (e.g., system, device, etc.) to detect and/or monitor one or more factors relevant to a patient's health. When using a soft-tissue sensor to monitor patient health it may be helpful to hold the sensor, and particularly a microneedle associated with the soft-tissue sensor in stable contact with the soft tissue. Described herein are intraoral, soft-tissue sensor systems that may be used to hold a soft tissue sensor in contact with the gingiva.

In general, the soft tissue sensor systems described herein may include an intraoral appliance shaped to receive a patient's teeth within a cavity and to secure the intraoral appliance against the patient's teeth. The intraoral appliance may be configured to fit snugly over all or a portion of a patient's teeth in the patient's upper or lower arch. The cavity in the intraoral appliance may be formed as a negative of the patient's dentition in the patient's upper or lower arch. The intraoral appliance may be formed of any appropriate material (including polymeric material, and clear or transparent materials), and may be formed in any appropriate manner. For example, the intraoral appliance may be fabricated by a lamination technique (e.g., vacuum forming), or by an additive (e.g., 3D printing) method or casting into a mold or by milling from a block of appropriate material. A combination of multiple such fabrication techniques may also be used.

In general, the intraoral appliance is configured to hold a soft tissue sensor, and may therefore include a mount to secure the soft tissue sensor in or on the intraoral appliance. The mount may include a lock or other securement to hold the soft tissue sensor in place. Any of the soft tissue sensor systems described herein may optionally include a soft tissue sensor that is mounted to the intraoral appliance, e.g., in a soft tissue sensor mount. The soft tissue sensor may include one or more microneedles that will project from the intraoral appliance when the soft tissue sensor is coupled with the intraoral appliance. The microneedles may be configured to penetrate soft tissue adjacent to the patient's teeth when the intraoral appliance is worn on the patient's teeth. As mentioned, any appropriate soft tissue sensor may be used. In general, the soft tissue sensor may be configured to detect at least one analyte through the one or more microneedles.

Figure 1A:
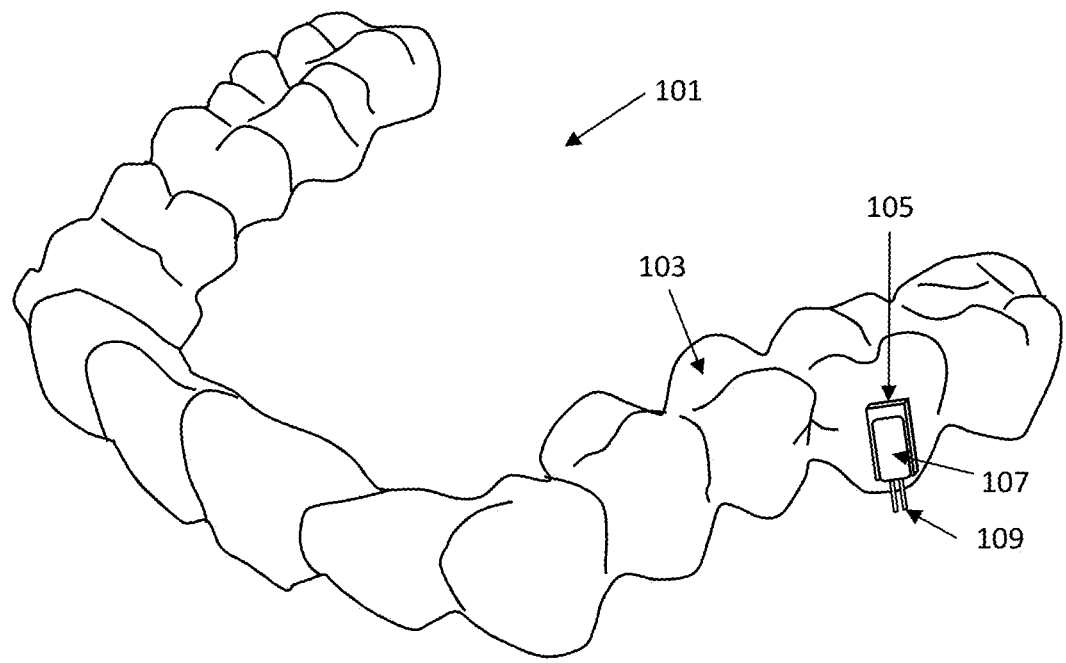
FIG. 1A is a is an example of an apparatus configured as an intraoral, soft-tissue sensor system, including an intraoral appliance shaped to receive a patient's teeth and to secure the intraoral appliance against the patient's teeth, and a soft tissue sensor mounted to the intraoral appliance, wherein the soft tissue sensor comprises one or more microneedles projecting from the intraoral appliance that are configured to penetrate soft tissue adjacent to the patient's teeth when the apparatus is worn.

For example, FIG. 1A shows an example of a soft tissue sensor system 101. The soft tissue sensor 107 shown in this example is held in a sensor mount 105 that is formed in or connected integrally with, the intraoral appliance 103. In the example shown in FIG. 1A, the soft tissue sensor includes two microneedles that extend way from the intraoral appliance, towards the gingiva, so that the microneedles may contact the gingiva when the soft tissue sensor system is worn on the patient's teeth.

Figure 1B:
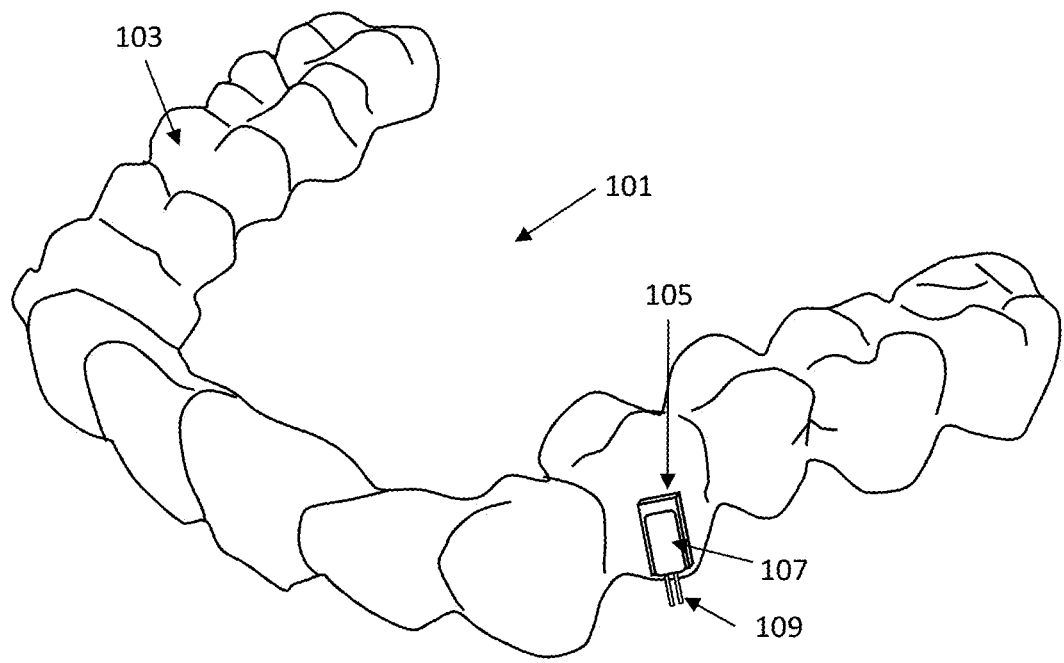
FIG. 1B is another example of an apparatus, similar to that shown in FIG. 1A, in which the sensor is held in a mount on the intraoral appliance in a second location, different from the first location shown for the mount and sensor in FIG. 1A.

In FIG. 1A, the intraoral appliance includes the sensor mount 105 that is fixed on or in the intraoral device 103 on the left side in the second-from-the-last molar. FIG. 1B shows another example of a soft tissue sensor systems including an intraoral appliance, similar to the one shown in FIG. 1A, only positioned at a difference location. In FIG. 1B, the soft tissue sensor mount 105' is attached to the intraoral appliance 101' on the first (most anterior) molar on the buccal side of the teeth.

Note that in any of the soft tissue sensor systems described herein, the intraoral appliance may be formed or customized to the patient who will be wearing the apparatus.

In addition, any of the soft tissue sensor systems described herein may include a bias (e.g., coupled to the soft tissue sensor and/or a portion of the soft tissue sensor that is configured to apply a biasing force to the soft tissue sensor.

FIGS. 2A-2D illustrate examples of different soft tissue sensor mounts, each shown holding a soft tissue sensor with one (e.g., FIGS. 2C and 2D) or more, e.g., two, microneedles in communication with the sensor. The sensor may also include control logic (e.g., hardware, software firmware, including a microcontroller to coordinate the collection and distribution of data, one or more processors for processing the data, a memory for storing the data, wireless communication circuity as well as wireless circuitry for transmitting/receiving information.

In FIG. 2A, an example of a sensor holder 205 is shown with the soft tissue sensor 207 held (shown as removably held In FIG. 2A) in the sensor holder. The sensor holder may include a cavity or opening that is sized to snugly fit and hold a soft tissue sensor 207 in a fixed position, even with movements of the jaw. The sensor holder opening may be configured to hold a standard-sized sensor, or it may be custom-made to fit a specific soft tissue sensor. In FIG. 2A, the sensor is roughly rectangular with two microneedles 209 extending from the base of the sensor and out of the holder so that they may engage with the target, e.g., the gingiva. In FIG. 2A, the cavity of the sensor mount 205 may be made of a material that is slightly compressible so that the opening of the sensor mount into which the sensor is pushed, to engage the sensor in the sensor mount, may be slightly smaller than the sensor. The sensor may deflect the perimeter of the opening slightly to fit into the cavity of the sensor mount, which may then return to the original size, retaining the sensor within the cavity, which may be approximately the same size, or slightly larger, than the sensor body.

FIG. 2B shows a sensor mount 205' that includes a bias 211 that may drive the microneedles 209 and/or the sensor 207 down, towards the gingiva, to make and/or maintain contact with the soft tissue. In FIG. 2B, the outer surface of the mount is not shown; however a cover may be used (see, e.g., FIG. 2C), or it may include an opening, similar to that shown in FIG. 2A. In FIG. 2B, the bottom of the mount 213 may be deformable and/or made form an elastic material, as shown. This may allow the bias element to deflect the bottom portion (as shown) downward, driving the microneedles down; the force applied by the bias 211 may be greater than the restoring force provide by the bottom cover portion. The bottom cover may be an elastic band or gasket around the perimeter of the mount, and may include an opening or openings for the microneedles or may pass around them, or may be pierced by the microneedles. As will be described in more detail below, the bias may be triggered (e.g., by pushing on the front surface of the holder or a button on the front surface) to drive the microneedles down, e.g., into the gingiva.

FIG. 2C shows another example of a mount 205" for a soft-tissue sensor, or a portion of a soft tissue sensor including a microneedle, similar to that shown in FIGS. 2A-2B. In FIG. 2C, the cover may be removable or integral with the mount. The soft-tissue sensor in this example includes a single microneedle that extends down, e.g., towards or into the gingiva.

In any of these variations, the soft tissue sensor may include a probe, rather than, or in addition to, a microneedle. For example, the soft tissue sensor may include one or more electrical probes that extends down to or into the gingiva, in order to transmit and/or receive electrical signals from the tissue. Alternatively, the microneedle may be configured as a probe.

Alternatively or additionally, the bias may be configured to permit a microneedle/probe to push up on the sensor, without penetrating the soft tissue, while maintaining the probe in good (e.g., electrical) contact with the tissue. For example the bias on the upper side of the mount may provide only a very low level of force, so that the pressure on the microneedle or probe may be less that that required to penetrate the tissue. FIG. 2D shows an example of a mount 205''' that is configured to "float" the non-penetrating microneedle (configured as a blunted probe 209' having an enlarged, rounded tissue-engaging bottom) against the gingiva. The mount in this case include the soft biasing element 211' and a deformable (e.g., in this example, elastically deformable) bottom 213'.

In some variations, the sensor itself (without necessitating a separate 'probe' or needle portion) may be drive against the soft tissue when held by the intraoral appliance. For example, the senor may include a sensing surface (e.g., electrode, etc.). The bias on the intraoral soft tissue sensing system may drive the sensor against the soft tissue.

The soft tissue sensors shown corresponding to the mounts shown in FIGS. 2A-2D are exemplary only. The shape and size of the soft tissue sensor may be different. The mount may be configured to hold the entire sensor, or a portion of the sensor, and particularly the portion including the microneedles, and may include a bias, as shown. Alternatively, the soft tissue sensor may be held in multiple mounts, any of which may include a bias. In some variations the mount may apply the biasing force to the soft-tissue sensor and/or to the microneedles specifically.

In general, any of the sensors described herein may include a non-penetrating microneedle, which may be referred to as a probe, that is configured to be in contact with the soft tissue without penetrating the tissue. FIG. 2D, described above, shows on example of this. Any number of such non-penetrating microneedles (probes) may be used for a particular sensor, and the probe may be configured to contact the surface of the tissue without penetrating. The sensor may be configured to include multiple sensing features, including electrical (e.g., conductance, resistance, etc.), mechanical (vibration, deflection, etc.), chemical, thermal (temperature sensing, etc.), or the like.

In any of these variations, the outer surfaces of the mount may be configured to form a smooth and/or continuous surface with the intraoral appliance. Any of these mounts may be formed integrally with the intraoral appliance, or they may be separately attachable to the intraoral appliance.

Figure 3C:
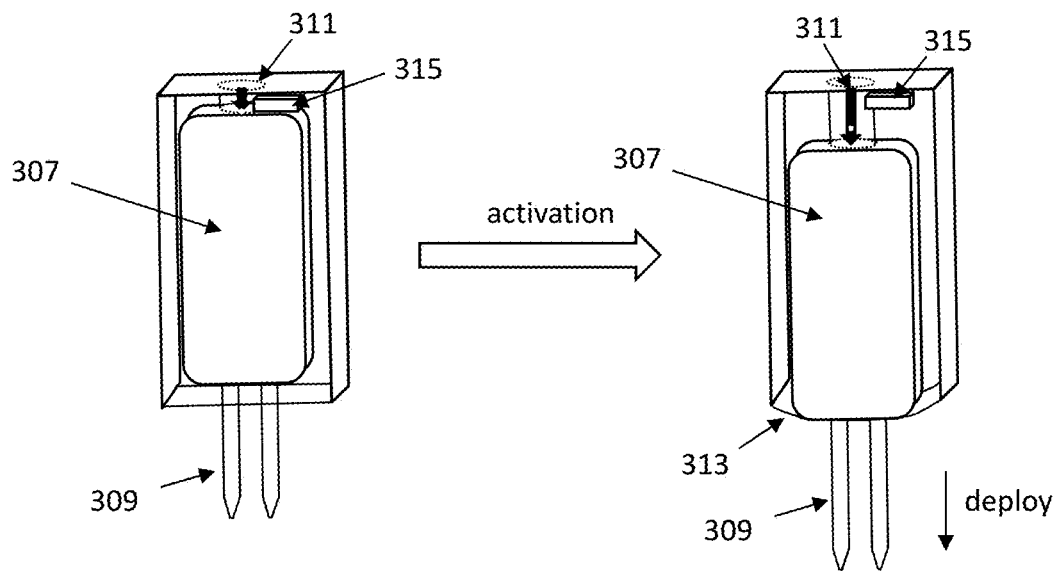
Figure 3C:
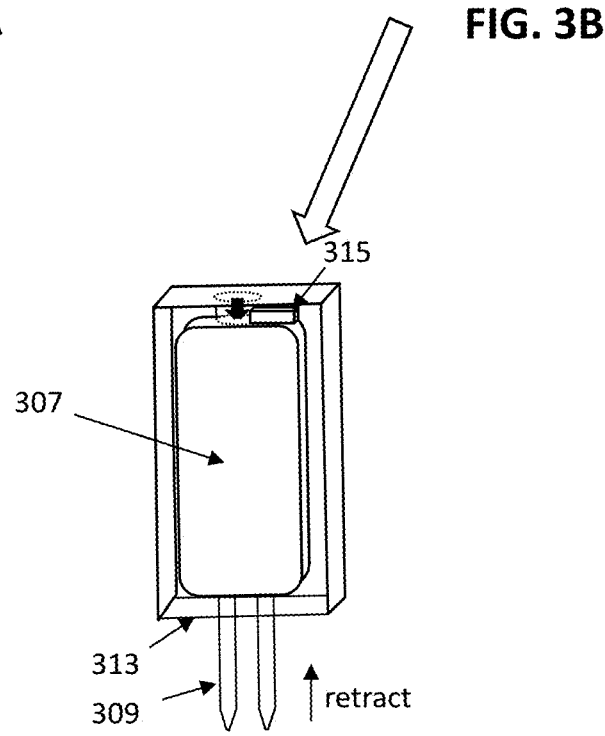

As mentioned above the biasing in any of these variations may be configured to be activatable, so that a basing force (e.g., driving the microneedle(s) and/or sensors down into or onto the tissue) may be applied only after activating the device, e.g., when the device has been seated onto the patient's teeth. FIGS. 3A-3C illustrate an example of an activatable bias. In this example, similar to the variation shown in FIG. 2B, above a sensor 307 is shown in the mount 305. Initially, the bias 311 is not engaged, and is not applying a force against the senor/microneedles 309 (see FIG. 3A). The mount may include a cover (not shown). In this example the bottom surface of the mount may also be formed of an elastically deformable material, as described in FIG. 2B. A deployment control (e.g., button, trigger, switch, etc.) may be included as part of the mount. In FIG. 3A, the deployment control is shown as a button 315 on the face or front of the mount (e.g., on the cover or outer surface). Alternatively, the deployment control may be electronic/electric and may receive an activation signal remotely (e.g., from an application software in communication with the sensor and/or mount), or it may be located on an inner surface of the mount or within the cavity (including near the occlusal surface of the cavity, so that the bias will be automatically deployed when the apparatus is seated on the teeth. In FIG. 3A, the bias may be deployed (e.g., released) by pushing on the button 315, allowing the bias to activate, as shown in FIG. 3B. In FIG. 3B, the bias 311 is pushing against the elastically deformable bottom 313 of the mount, driving the microneedles 309 down into a deployed configuration. Note that the extent of deployment (e.g., the length that the microneedles are extended by the bias) may be any appropriate length, which may be set by choosing the geometry of the bias, as well as the elastic properties of the bottom of the mount.

The microneedles may be retracted by disengaging the bias 311, as shown in FIG. 3C. The bias may be disengaged by another control, or by the same control 315, which may retract the needles, or allow them to retract based on the elastic properties of the bottom of the mount. For example, the bias may be retracted by moving it up, away from the sensor, by collapsing it back down, or by otherwise releasing the biasing force.

In general, any appropriate bias may be used, including mechanical (e.g., spring, coil spring, leaf spring, etc.), electrical/magnetic (e.g., solenoid, electromagnet, etc.), pneumatic, liquid, etc. The type of bias chosen may determine the activation/inactivation means used.

Figure 4:
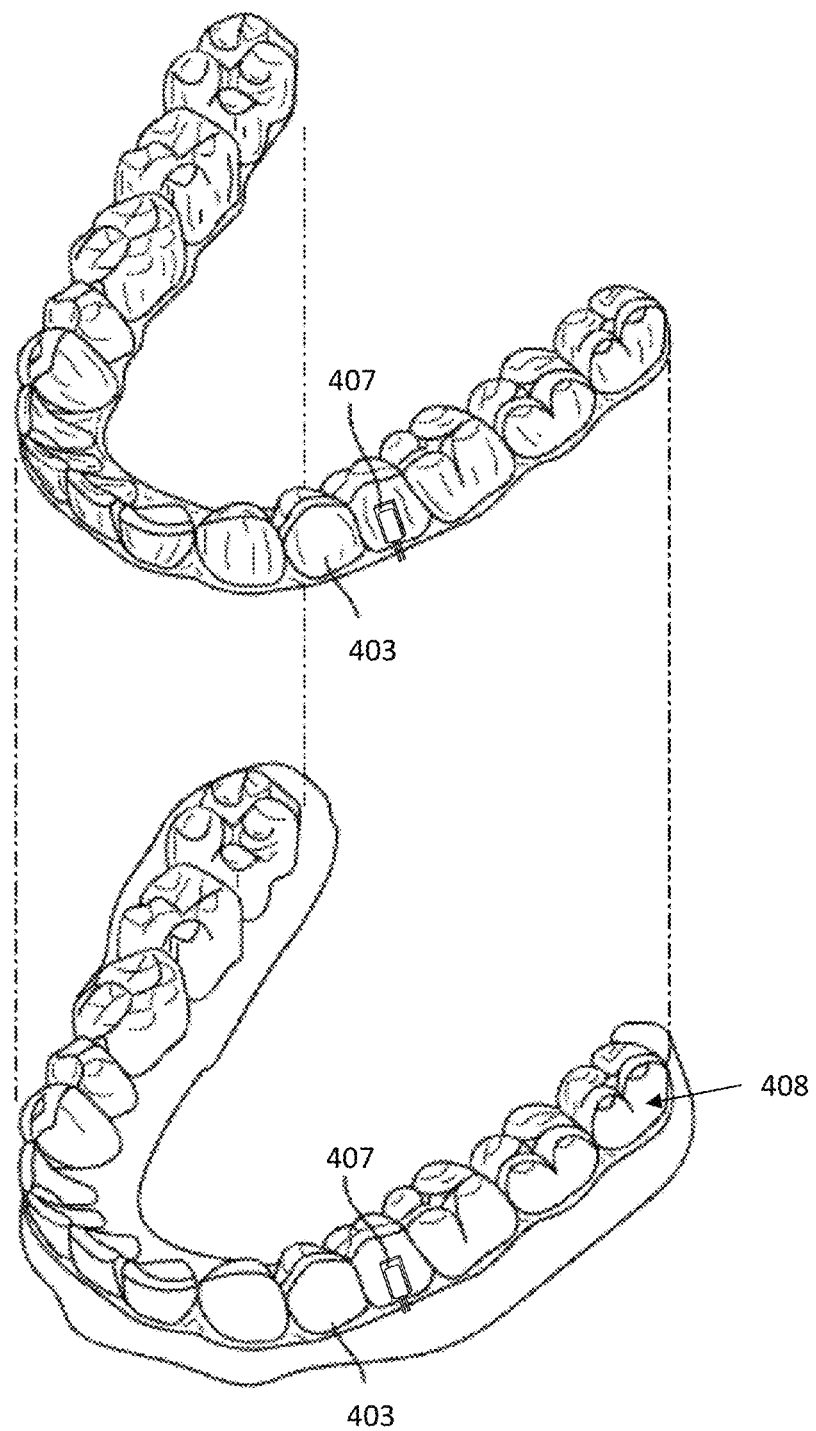
FIG. 4 illustrates the application of an apparatus such as that shown in FIG. 1A or 1B onto the patient's teeth, so that when secured onto the teeth, the sensor and microneedle may be in contact with the gingiva.

FIG. 4 illustrates the application of an intraoral, soft-tissue sensor system onto a subject's teeth 408. A sensor 407 is mounted into the intraoral appliance forming the intraoral, soft-tissue sensor system 403, and the teeth fit snugly into the cavity formed by the intraoral appliance, which is shown as transparent in this example. The apparatus may be worn so that the microneedles of the sensor are inserted into or onto the gingiva, as shown, to provide monitoring, including continuous monitoring for one or more analyte, depending on the sensor configuration. The methods and apparatuses described herein may be generic to a variety of different sensors, and may provide a platform for stably holding a sensor having a probe or microneedle relative to the gingiva, by connecting to the hard tissue of the patient's teeth. The intraoral, soft-tissue sensor systems described herein may therefore provide a comfortable platform for measuring from the soft tissue.

Figure 5A:
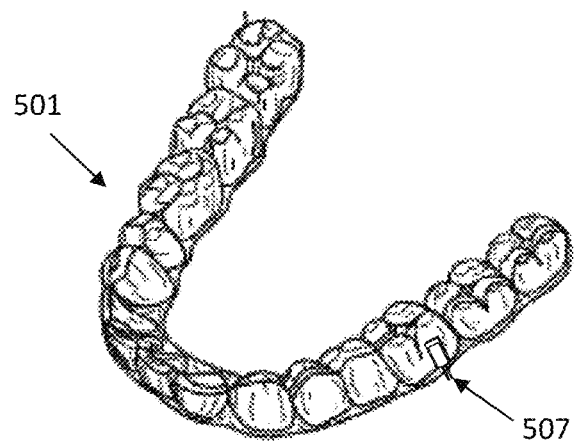
FIGS. 5A-5C illustrate a series of apparatuses such as those shown in FIGS. 1A and 1B, in which the sensors are arranged in different locations. The devices shown in FIGS. 5A-5C may be worn sequential (e.g., the device of FIG. 5A, then FIG. 5B, then FIG. 5C may be worn sequentially).
Figure 5B:
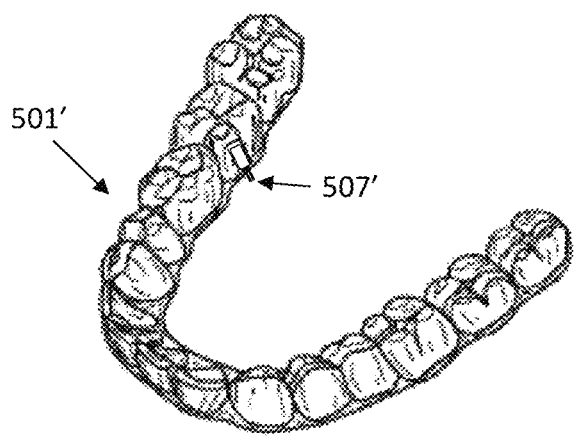
Figure 5C:
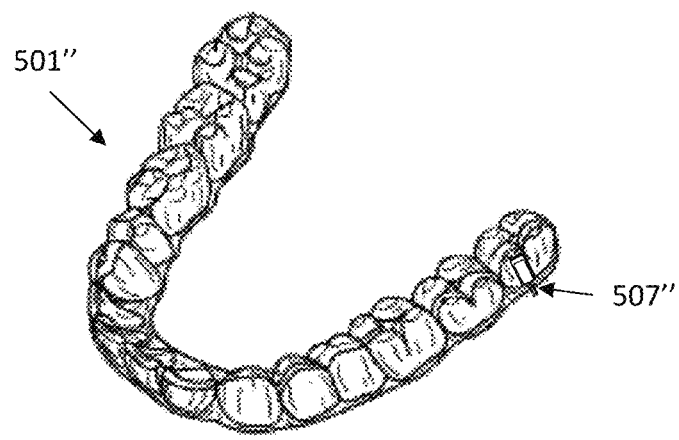

Long term monitoring may be possible with any of the intraoral, soft-tissue sensor systems described herein. In particular, any of the methods and apparatuses described herein may include a series of intraoral, soft-tissue sensor system that may be worn sequentially, as shown in FIGS. 5A-5C. In this example, the sensor 507 may be mounted at different locations. Thus, at different times, the microneedle/probe(s) of the sensor may be interacting with different regions in the oral cavity soft tissue. This may reduce or eliminate irritation and prevent harm to the tissue. For example, the first apparatus 501 may be worn for a first time period (1 hour, 2 hours, 3 hours, 4 hours, 6 hours, 12 hours, 24 hours, 36 hours, 2 days, 3 days, 4 days, 5 days, 6 days, 1 week, 2 weeks, 3 weeks, etc., preferably 1-3 days), the switched and the second apparatus 501' may be worn. The sensor in the second apparatus is on a different portion of the intraoral appliance. Again, after a second time period, a third apparatus 501" may be worn. This process may be repeated with as many apparatuses as desired. The apparatuses may be reused (e.g., as part of a repeating cycle), with cleaning between use. The patient may insert and remove the devices themselves, without the need for a physician or technician.

Alternatively, the same apparatus, which may be configured to move the mount for the sensor and/or may have a plurality of mounts on the intraoral appliance body, may be used. After the desired wearing time period, the apparatus may be removed from the patient's mouth and the sensor(s) moved to a different location on the apparatus.

Figure 6:
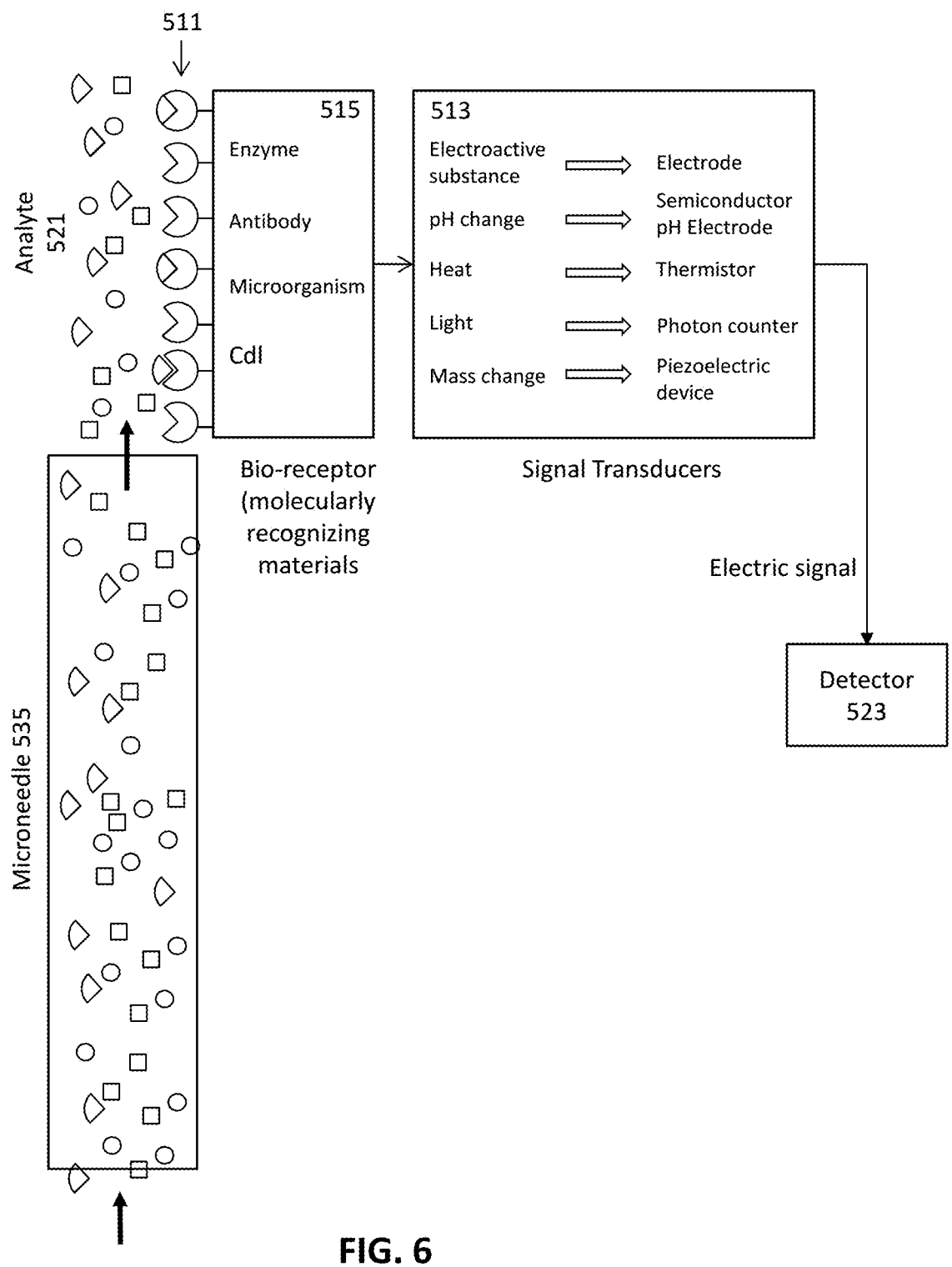
FIG. 6 is a schematic illustrating one example of a sensor (including a microneedle, shown as a hollow microneedle) that may be used to sense one or more analytes. The soft tissue sensor includes a bio-receptor portion for recognizing the analyte, and a signal transduction portion for transducing the signal sensed, and a detector for indicating that a signal (and optionally the intensity of the signal) representing the analyte has been detected.

As mentioned above, any appropriate sensor may be used. For example the sensor may be configured with a hollow microneedle (or multiple hollow microneedles), a bio-receptor portion to bind and/or otherwise interact with a target analyte and a signal transducer to convert the binding/interaction into a discernable signal that may be converted into an electrical output and sent to a detector, for further processing. FIG. 6 illustrate a schematic example of such a sensor. In this example, the microneedle 535 is hollow and allows passage of a fluid (e.g., blood, lymph, interstitial fluid, etc.) containing one or more analyte 521 into a sensing region 515 that include a bio-receptor 511 that interacts with (e.g., binds) the analyte and triggers a signal transduction event. For example, the bio-receptor may be an enzyme, antibody, microorganism, Cdl, etc. that may alter its properties (including optical, chemical, electrical, or other measurable properties) or trigger a detectable change 513 that transduces the interaction event.

Any of the apparatuses described herein may be configured as intraoral (or "oral") sensors that may be held in continuous contact with the soft tissue, such as the gums (gingiva), and/or palate. These apparatuses may include or be configured for use with one or more microneedles that may be immersed in the tissue or may contact the tissue. Microneedles may be used to measure passively, deliver signals actively, and/or deliver and extract materials from and to the body. Typically, the sensor may be held in place via an appliance attached to the teeth. A bias, such as a spring (or spring-like) mechanism may be used to apply a continuous force on the senor to keep the sensor in place, as described above. The sensor may be detachable (from the appliance) and may optionally be configure so as to not interfere with the patient's bite. Additionally the apparatus, including the sensor or a portion of the sensor may be formed of a transparent and/or translucent material. Any of these apparatuses may be configured so that they may be supported in the mouth using a mini implant (e.g., TAD), and/or a screw to a prosthetic tooth, and/or an attachment on one or more of the patient's teeth.

For example, any of the apparatuses described herein may be configured to actively apply energy (e.g., current) to the soft tissue via one or more contacts, including the microneedle/probes described herein. Thus, a sensor included as part of the intraoral, soft-tissue sensor systems described herein may be configured to deliver/transmit a stimulation, including (but not limited to) electrical stimulation. For example, a sensor may be configured to transmit a low level current to the soft tissue. A current may be applied, for example, to activate the patient's senses and/or to directly activate the patient's muscles. This may be therapeutically useful to treat snoring or apnea in variations configured to detect snoring or apnea, as it may encourage or cause the airways of a sleeping patient to open, e.g., when snoring. Other materials, including drugs, or active chemical agents, may be released by the apparatus in response to a sensed condition. One or more drugs could be delivered from the same needle (e.g., microneedle) used for sensing, or a separate one or more microneedles could be used. For example, a sensor configured to detect a patient condition such as insulin level in a diabetic patient wearing the device could be administered a small amount of insulin through the same of a different microneedle in contact with the soft tissue within the oral cavity. This may allow both continuous glucose monitoring (e.g., via a sensor and microneedle(s)) and potentially may allow immediate delivery of insulin via the same apparatus. Alternatively, the intraoral system may communicate with (or include) a separate drug pump for delivery of drug (e.g., insulin, etc.).

Any of the apparatuses described herein may be configured to deliver a drug, including in particular, delivering a drug based on a sensed need for the drug.

In addition, the apparatuses described herein may be configured to sense from other portions of the patient's oral cavity, in addition or instead of the soft tissue. For example, the sensors used may include sensors configured to measure or detect air flow due to inhaling and exhalation, and/or may analyze the inhaled gas and warn for toxic or harmful substances, and/or may analyze air exhaled by the patient and warn for issues that may be detected by sensed analytes, and/or analyze breath rates, pacing, etc., and/or detect and warn of halitosis, and/or detect alcohol level.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

For example, any of the sensors described herein may be configured to communicate in one-way or two-way communication with a remote (e.g., external) device, such as an external processor (e.g., smartphone, computer, wearable electronics, pad, etc.). Alternatively or additionally, any of these sensors may be configured to communicate with a processor on or in the intraoral appliance. The communication may be via a wired connection or a wireless connection; the processor in/on the intraoral appliance may store, modify, and/or send/receive data from the sensor. Thus any of these sensors and/or components in the intraoral soft tissue sensor system (including a processor or processors) may include wireless communication circuitry (e.g., WiFi, Bluetooth, Zigbee, etc.). Any of these apparatuses may also include power (e.g., battery, power control circuitry, inductive power/charging, etc.).

EXAMPLES

Any of the soft tissue sensors including one or more microneedles described herein may be used with or integrated into an orthodontic apparatus as described herein and may include a sensor (e.g., biosensor) configured to be positioned in a subject's oral cavity, including but not limited to a soft tissue, and an electronics system in communication with the sensor, where the electronic system includes one or more of: a signal amplifier, a signal conditioner (e.g., filter, averaging, etc.), processor, memory (e.g., data logging unit), power source (e.g., battery, capacitor, etc.) and data communications (e.g., wired or wireless communications, such as Bluetooth, Wifi, Zigbee, RFID, ultrasound, or the like). The sensor may convert a biomarker detection into an electrical signal, and may include a bioreceptor and a biotransducer. The bioreceptor may be configured to interact with a specific analyte or subset of analytes and produce a measurable signal (optical, chemical, mechanical, thermal, electrical, or some combination of these) that is transduced by the biotransducer into an electrical signal that can be processed (amplified, filtered, averaged, combined, etc.) by the electronic subsystem. The electronic subsystem may be an integrated system (e.g., a CMOS-based microprocessor). All or some of these components may be on or part of an oral appliance, such as an aligner, brace, palatal expander, etc.

Figure 7A:
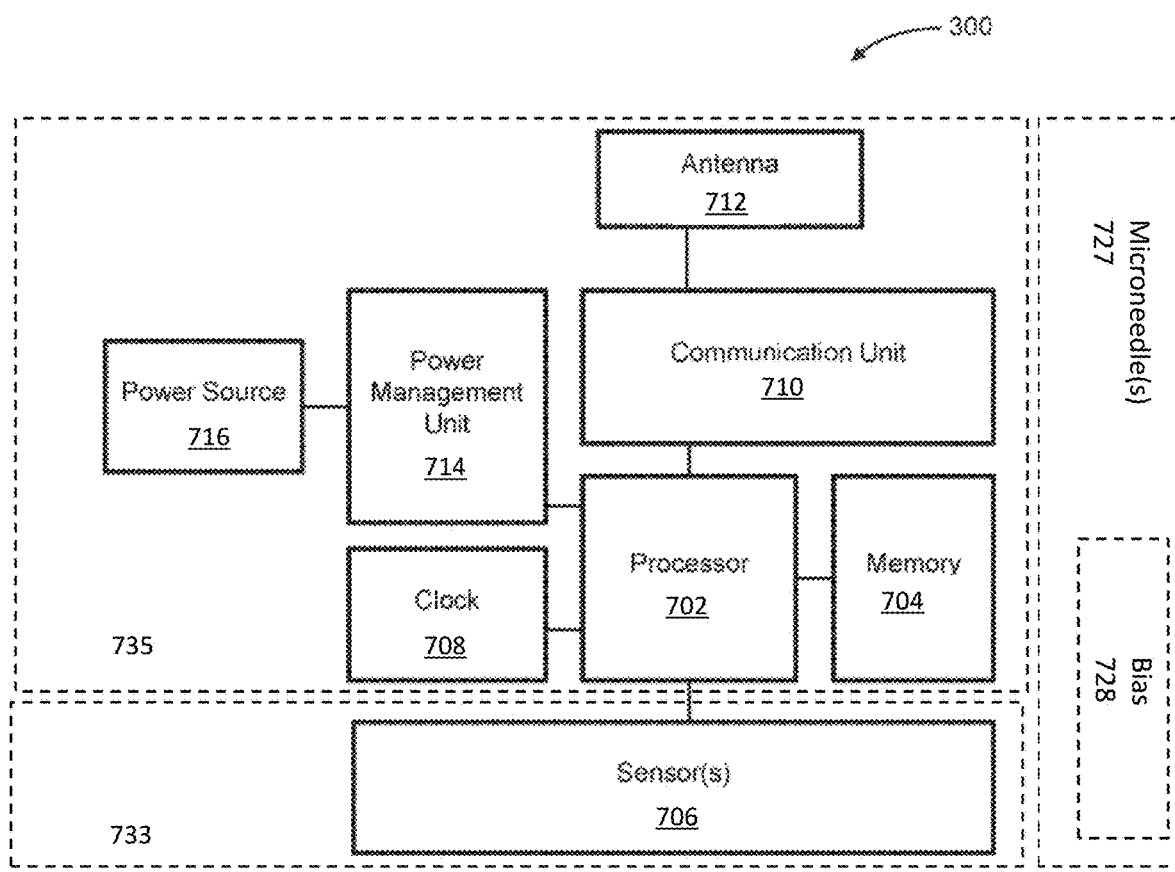
FIG. 7A schematically illustrates one example of an apparatus including a monitoring device (e.g., electronics) that may include a biosensor or may communicate with a biosensor coupled to the oral cavity (e.g., teeth, gingiva, etc.) and one or more microneedle(s).

For example, FIG. 7A shows a portion of an apparatus that includes a biosensor (sensor(s) 706) comprising a bioreceptor and biotransducer, in communication with an electronics system 735. The biosensor may be integrated and/or incorporated with the electronics system 735 and connected directly to a patient, etc., on a tooth, teeth, gingiva, etc., or it may be connected to an oral appliance. The biosensor(s) 733 may be separate from the electronics system 735 (indicated by the dashed lines. For example, the biosensor(s) may be part of a second oral appliance and/or directly mounted in the oral cavity (e.g., on a tooth/teeth), and may couple to an oral appliance including all or some of the electronics system (e.g., battery/power source 716, processor 702, antenna 712, memory 704, etc.). The biosensor may include any of the microneedles projecting from the intraoral appliance that are configured to penetrate soft tissue adjacent to the patient's teeth when worn and in some variation a bias coupled to the soft tissue sensor configured to apply a biasing force to the soft tissue sensor. The microneedles may be part of the biosensor 733 or part of the electronics system 735, or both.

Figure 7B:
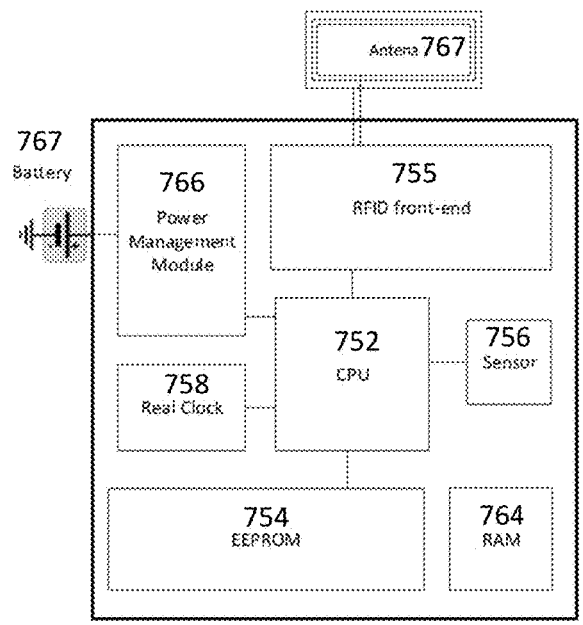
FIG. 7B schematically illustrates another example of an apparatus including a biosensor that may include any of the microneedles described herein.

FIG. 7B is another example of a schematic illustrating a biosensor apparatus. In FIG. 7B, the biosensor(s) 756 are integrated with the electronics system. The electronics system in this example include a processor (CPU 752) that may amplify, filter, analyze and/or store the signals from the biosensor(s). The biosensor(s) may include a bioreceptor and a biotransducer that converts interaction (e.g., binding, enzymatic interaction, etc.) with a biomarker into an electrical signal. The electronics may further include an oscillator/clock 758, and a memory (e.g., EEPROM 754). Additional memory (e.g., RAM 764) may also be included. The memory may store data generated by the biosensor(s) and/or control logic/command logic for operating the apparatus.

This logic may be modified (e.g., programmable). Additional memory the electronics system (which may also be referred to herein as a sensor electronics system or subsystem) may include communications circuitry (shown as an RFID front end 755) in FIG. 7B, which may also include or communicate with an antenna 757. The electronics system may also include power management circuitry 766, for regulating the power used by the electronics and/or biosensor(s). The power management circuitry may regulate a power source, such as a battery 767.

Figure 8A:
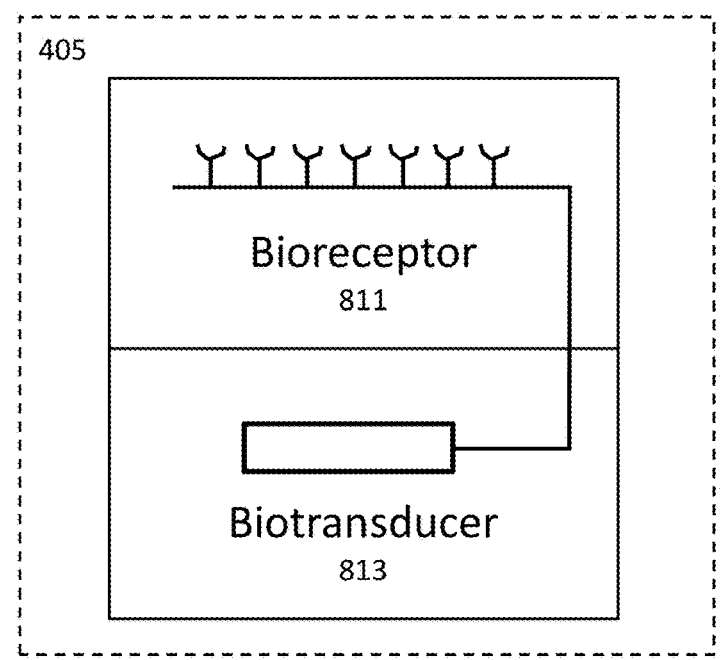
FIG. 8A illustrates a schematic of a biosensor apparatus (e.g., which may be part of a monitoring device) with an activation mechanism that may include any of the microneedle(s) described herein.
Figure 8B:
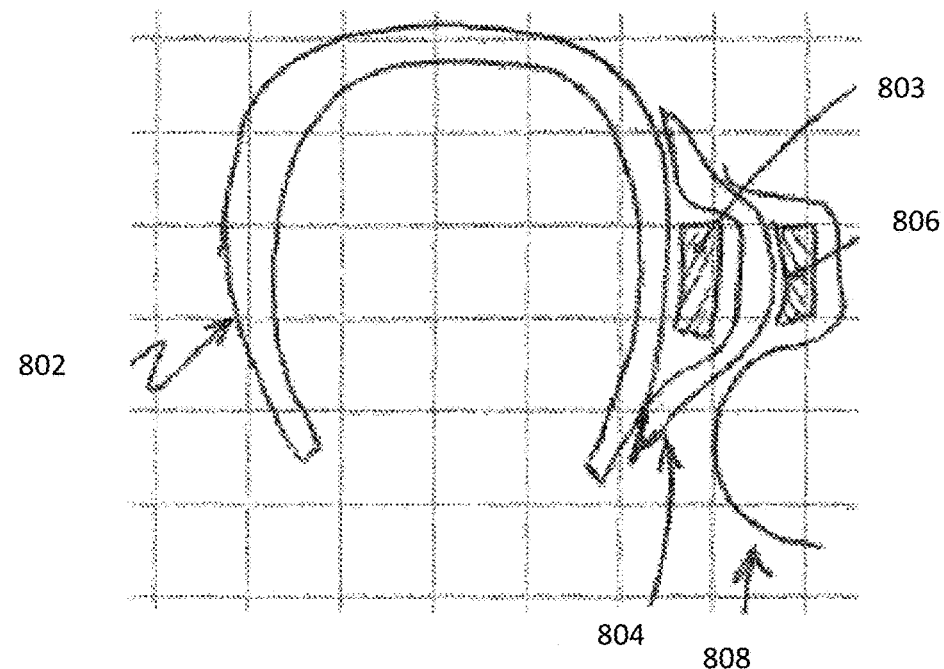
FIG. 8B illustrate schematically an example of a monitoring device 800 with an activation mechanism that may include any of the microneedle(s) described herein.
Figure 8C:
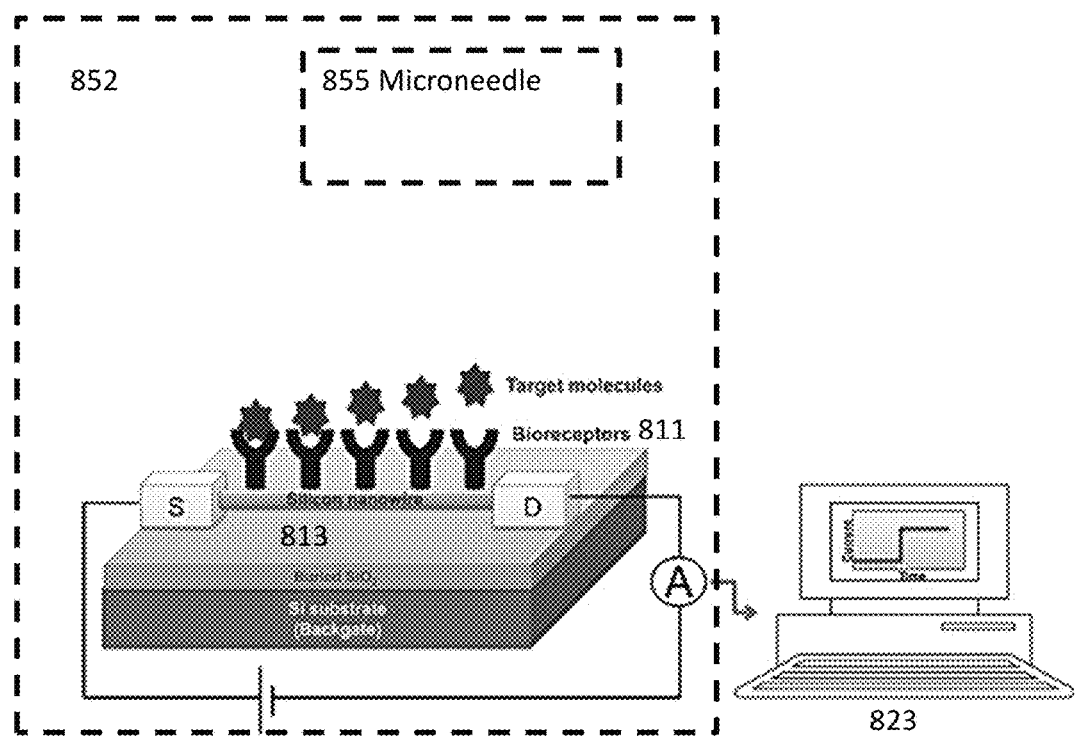
FIG. 8C is an example of an apparatus with an activation mechanism similar to that shown in FIG. 8A. In this example, the apparatus includes one or more microneedles, and one or more bio-receptors formed on a silicon nanowire atop a substrate. Nanoparticles and/or nanowires may be used as part of the bio-receptor and may be included at least partially in or in fluid communication with the one or more microneedles.

As schematically illustrated in FIG. 8A, a biosensor 405 may include a bioreceptor 811 that interacts with a biomarker and is functionally coupled with a biotransducer 813. In this example, the bioreceptor is shown schematically including specific interaction sites that may engage with a biomarker, e.g., by binding, enzymatically reacting with, etc. The biotransducer 813 is functionally linked to bioreceptor and may transduce interaction between the biomarker and the bioreceptor into an electrical signal (output) that is passed on to the electronic system (not shown, see, e.g., FIGS. 7A and 7B). For example, the biotransducer may bind to the bioreceptor and binding may be detected by the biotransducer via an optical signal. In some variations, the bioreceptor may be bound to an optically transparent substrate through which light may be passed by the biotransducer; a change in the optical properties of the bioreceptor may correlate with binding of the biomarker to the biotransducer. Alternatively, the bioreceptor may include a matrix (e.g., hydrogel) that interacts with the biomarker to modify a property of the matrix (e.g., electrical resistance, optical absorption, electrochemical potential, etc., and this modified property may be polled and/or detected by the biotransducer. Other specific examples are provided below. A microneedle may project from the intraoral appliance and/or from biosensor.

Any appropriate biomarker or biomarkers may be used. Biomarkers may be biomolecules or byproducts of biomolecules that are present in the oral cavity (including saliva, GCF, and/or breath) and/or contaminants that may be present in the oral cavity, such as bacteria, yeast, etc. Biomolecules of particular interest include those that change in response to movement of the teeth due to an orthodontic procedure. For example, Table 1, below lists examples of biomarkers that may be tested using the biosensor apparatuses described herein. For example in Table 1, protein biomarkers include Protein S100-A9 (e.g., S100 calcium-binding protein A9, Calgranulin-B), Serum albumin precursor, Immunoglobulin J chain, Ig alpha-1 chain C region, Cysteine-rich secretory protein 3 precursor (CRISP-3), Hemoglobin subunit beta (Hemoglobin beta chain, Beta-globin), and 14-3-3 protein σ (Stratifin, Epithelial cell marker protein 1).

TABLE 1

Summary of saliva proteins with expression change during orthodontic treatment. (These are proteins that show statistically significant change (P < 0.5) between day 0 and day 14 of orthodontic treatment.)

| Spot no. | Protein name | Known Function | Accession number (UniProt) | MW (kDa)/pI Theoretical | MW (kDa)/pI Experimental | Peptides matched/% coverage (Protein score) | Expression change |
|---|---|---|---|---|---|---|---|
| 1 | Protein S100-A9 (S100 calcium-binding protein A9) (Calgranulin-B) | (i) Calcium-binding protein. (ii) Promotes phagocyte migration and infiltration of granulocytes at sites of wounding. (iii) Plays a role as a proinflammatory mediator in acute and chronic inflammation. | P06702 | 13.2/5.71 | 14.5/5.47 | 4/24% (121) | Down regulated at day 14 |
| 2 | Serum albumin precursor | (i) Good binding capacity for water, Ca2+, Na+, K+, fatty acids, hormones, bilirubin, and drugs. (ii) Main function is the regulation of the colloidal osmotic pressure of blood. (iii) Major zinc transporter in plasma. | P02768 | 69.3/5.92 | 14.8/7.00 | 8/11% (105) | Down regulated at day 14 |
| 3 | Immunoglobulin J chain | (i) Serves to link two monomer units of either IgM or IgA. (ii) Help to bind IgM or IgA to secretory component. | P01591 | 15.5/4.62 | 34.0/3.86 | 10/30% (220) | Down regulated at day 14 |
| 4 | Immunoglobulin J chain | | P01591 | 15.5/4.62 | 36.4/3.40 | 6/27% (198) | Down regulated at day 14 |
| 5 | Ig alpha-1 chain C region | (i) Major immunoglobulin class in body secretions. (ii) Serve both to defend against local infection and to prevent access of foreign antigens. | P01876 | 37.6/6.08 | 44.76/6.91 | 9/20% (260) | Down regulated at day 14 |
| 6 | Cysteine-rich secretory protein 3 precursor (CRISP-3) | (i) Innate immune response (ii) Potential biological marker for prostate cancer | P54108 | 27.6/8.09 | 43.25/8.90 | 2/6% (94) | Present only at day 14 |
| 7 | Hemoglobin subunit beta (Hemoglobin beta chain) (Beta-globin) | Involved in oxygen transport from the lung to the various peripheral tissues. | P68871 | 15.9/6.75 | 14.83/9.50 | 6/27% (158) | Present only at day 0 |

TABLE 1-continued

Summary of saliva proteins with expression change during orthodontic treatment. (These are proteins that show statistically significant change (P < 0.5) between day 0 and day 14 of orthodontic treatment.)

| Spot no. | Protein name | Known Function | Accession number (UniProt) | MW (kDa)/pI Theoretical | MW (kDa)/pI Experimental | Peptides matched/% coverage (Protein score) | Expression change |
|---|---|---|---|---|---|---|---|
| 8 | 14-3-3 protein σ (Stratifin) (Epithelial cell marker protein 1) | (i) Adapter protein. (ii) Binds to a large number of partners, generally results in the modulation of the activity of the binding partner. | P31947 | 27.7/4.68 | 44.76/4.20 | 5/22% (147) | Present only at day 0 |

Table 1: Gingival Crevicular Fluid (GCF) biomarkers (Table 1 is adapted from Ellias M F et al. "Proteomic Analysis of Saliva Identifies Potential Biomarkers for Orthodontic Tooth Movement". *The Scientific World Journal*. 2012; 2012: 647240. doi: 10.1100/2012/647240.)

Any of the apparatuses and methods described herein may target biomarkers present in gingival crevicular fluid (GCF), which may be collected by any of the microneedles described herein. In general, various molecules are capable of passing through gingival sulcular epithelium and may filter into GCF. Many of these molecules are associated with remodeling of paradental tissues during situations such as normal maintenances, periodontal diseases and Orthodontic treatment. The collection and analysis of GCF is a non-invasive procedure that may be useful information on the nature and extent of the periodontal response to mechano-theraphy and orthodontic treatments. The apparatuses and methods described here may be configured and/or adapted to collect GCF. For example any of the apparatuses described herein may include one or more microneedles projecting and extending between the teeth and gingiva (e.g., penetrating to a depth of 0.5 mm, 1 mm, 2 mm, 3 mm, 4 mm, 5 mm, 6 mm, etc.). The microneedle may be fixed or extendable as described above.

Modified or enhanced cellular activities during orthodontic tooth movement can be found in GCF of treated teeth. Additional biomarkers that may be examined, e.g., in GCF and/or saliva include prostaglandin E (PGE) (elevated prostaglandin E (PGE) levels in GCF 1 day after application of mechanical stimuli has been detected), cytokines, including IL-6 and IL-8, TNF-α, Hyaluronic acid, chondroitin sulphate, IGF, Acid phosphatase, Aspartate aminotransferase, Alkaline phosphatase (ALP), Lactate dehydrogenase, Collagenase, Matrix metalloproteinases (e.g., MMP-1, MMP-2 and MMP-8), Cathepsin B, TRAP, Osteocalcin, Osteonectin, Osteopontin and dentin sialoprotein. For example, a correlation has been found between the velocity of tooth movement and increase in concentrations of cytokine and its receptor antagonist. IL-6, IL-8 levels in GCF after force application has been shown. Increased level of TNF-α in GCF after force application which peaked at day 1 has been shown. Studies demonstrated elevated Hyaluronic acid in all GCF samples and chondroitin sulphate levels in GCF increased greatest in teeth that moved most. IGF (bone remodeling marker) may be elevated, and its binding protein levels in GCF, 4 h after mechanical stimulation. Acid phosphatase and Aspartate aminotransferase levels after force application are higher on compressed side compared to tension side in GCF. Alkaline phosphatase (ALP) levels are higher on tension side compared to compression side. Lactate dehydrogenase levels are higher on compression side whereas Collagenase levels are elevated on both mesial and distal sides after mechanical stimulus. Matrix metalloproteinases (MMPs) (MMP-1, MMP-2 and MMP-8) show elevated levels on compressed side than on tension side. Elevated levels of Cathepsin B, an indicator of ECM degradation, were demonstrated in GCF 1 day after force application. Elevated levels of TRAP in GCF on the compression side after force application has been shown. Osteocalcin, a bone turnover marker, may be elevated in GCF of patients with periodontal breakdown. Elevated levels of Osteonectin and Osteopontin have been detected in GCF with progressive increase in periodontal breakdown. Elevated levels of dentin sialoprotein in GCF samples of teeth at 12 weeks following commencement of fixed appliance therapy have also been demonstrated.

For example, the apparatuses and methods described herein may be configured to detect one or more of the following biomarkers. In some variations, these biomarkers may be detected from the saliva and/or the gingival crevicular fluid (GCF). These biomarkers may be particularly helpful in detecting tooth remodeling or movement. The levels of one or more of these biomarkers may be detected and tracked over the course of a treatment to adjust or modify an orthodontic treatment. For example, one of more markers for inflammation, remodeling and/or enzymes (e.g., enzymes associated with bone resorption, formation, cell necrosis, collagen remodeling, etc.) may be detected. Examples of makers for remodeling of the teeth may include: Glycosaminoglycans (e.g., in GCF), including hyaluronic acid and a minor band of chondroitin sulfate, Pyridinium derivatives (e.g., pyridinoline and deoxypyridinoline), Pentraxin-3, also known as tumor necrosis factor (TNF)-stimulated gene 14 (TSG-14), N-telopeptide type 1 and osteocalcin, Osteocalcin, and Matrix metalloproteins (MMPs) 1 and 8. Markers for inflammation may include: Prostaglandin E (PGE2), Neuropeptides (calcitonin related gene peptide and substance p), Transforming growth factor-α1, Epidermal growth factor (EGF), α2 Microglobulin (α2MG), insulin-like growth factor-1, Interleukin-1 (receptor antagonist) (IL-1) 1β, 2, 6, 8 cytokines, Tumor necrosis factor-α, Macrophages colony stimulating factors, TNF-related ligand receptor activator of nuclear factor-kappa ligand (RANKL) and its two receptors, receptor activator of nuclear factor-kappa (RANK), and osteoprotegerin (OPG), and Myeloperoxidase (MPO). Markers of root resorption may include: dentine matrix protein 1, dentin phosphoprotein (DPP), and dentin sialoprotein (DSP). Enzymes and enzyme inhibitors may include: Cathepsin B, Acid phosphatase (ACP) and alkaline phosphatase (ALP), β-Glucuronidase (βG), Aspartate aminotransferase (AST), and lactate dehydrogenase.

As mentioned above, any of the biosensors described herein may include a bio-recognition component, a biotransducer component, and electronic system which may include a signal amplifier, processor, data logging units and data communication unit. In some instances, transducers and electronics can be combined such as in CMOS-based microsensor systems. The recognition component may be called a bioreceptor, may use a biomolecule from organisms or receptors modeled after biological systems to interact with the analyte of interest. This interaction may be measured by the biotransducer which outputs a measurable signal proportional to the presence of the target analyte in the sample. The processor can log the raw or processed data in the memory unit or transmit it to a receiver. The system can work actively if energized with battery, super-capacitor, or an energy harvesting unit, or it may perform passively upon being energized via induction using an external device, such as cell phone.

In any of the biosensors described herein, the bioreceptor may be configured to interact with the specific analyte of interest to produce an effect measurable by the transducer. The bioreceptor may have a high selectivity for the analyte among a matrix of other chemical or biological components. While the type of biomolecule used may vary widely, biosensors may be classified according to common types of bioreceptor interactions involving, e.g., interactions such as: antibody/antigen, enzymes/ligands, nucleic acids/DNA, cellular structures/cells, or biomimetic materials. The bioreceptor may be configured to engage in one or more of these interactions (e.g., may include a bound or engineered antibody, enzyme, nucleic acid sequence, protein or engineered protein, etc.) in a localized manner that may be interrogated by or communicated to the biotransducer.

For example, a biosensor as described herein for use with an oral appliance may be configured to take advantage of an antibody/antigen interaction with one or more of the biomarkers described herein. Thus, the biosensor may be configured as an immunosensor. An immunosensor may utilize the very specific binding affinity of antibodies for a specific compound or antigen. The specific nature of the antibody antigen interaction is analogous to a lock and key fit in that the antigen will only bind to the antibody if it has the correct conformation (proper selection of primary and secondary antibodies). Binding events result in a physicochemical change that, in combination with a tracer, such as fluorescent molecules or enzymes, can generate a signal such as an elevation in voltage that can be detected by electronic components. Binding may be detected optically (e.g., by color, or transmission) and/or electrically.

Also described herein are biosensors that include enzymatic interactions. For example, analyte recognition may be enabled through: (1) an enzyme converting the analyte into a product that is sensor-detectable, (2) detecting enzyme inhibition or activation by the analyte, or (3) monitoring modification of enzyme properties resulting from interaction with the analyte. Since enzymes are not consumed in reactions, the biosensor may be used continuously. The catalytic activity of enzymes may also lower limits of detection compared to common binding techniques.

Other biosensing techniques that can be used may include detecting nucleic acid interactions, detecting epigenetic modifications, cell based, and tissue based detection.

As mentioned above, a biotransducer may be electrochemical, optical, electronic, piezoelectric, gravimetric, and/or pyroelectric-based.

Figure 9:
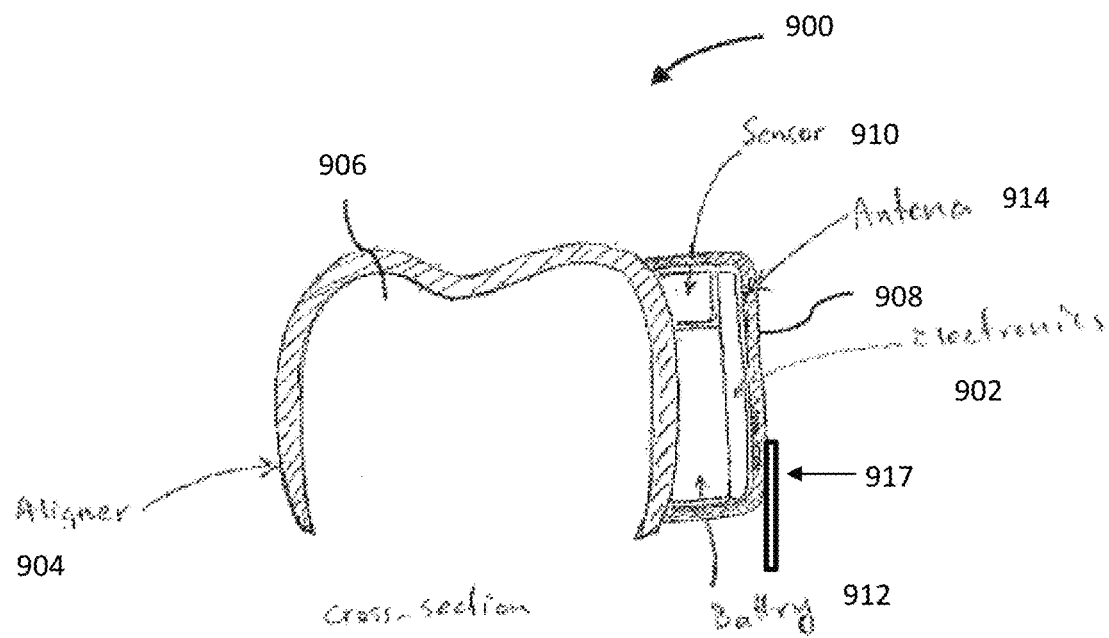
FIG. 9 is a cross-section through an apparatus similar to that shown in FIGS. 1A-1B (e.g., a removable orthodontic device, also referred to as an orthodontic appliance) including an integrated monitoring device and one or more microneedles.

FIG. 9 illustrate an example of an apparatus including a biosensor as described herein, similar to that shown in FIGS. 1A and 1B. For example, In FIG. 9, the apparatus 900 includes an orthodontic device, shown as an aligner 904 to which a biosensor or biosensors are coupled, either integrated into the housing of the electronics sub-assembly 902, or separate 951 but electrically connected to the electronics. The electronics (processor, battery, communications circuitry, antenna, etc.) is shown in a housing that mounted to an outside portion of the aligner, shown on the buccal side, although it may be on the lingual side instead or additionally. FIG. 9 shows an example of a section through an apparatus in which the biosensor (or a separate sensor 910, such as a temperature sensor or the like) is included with the electronics 902. An outer cover 908 may hold the assembly to the aligner 904 and the apparatus may be placed over the teeth 506. One or more microneedle 917 may extend or be extendable from the device. In some variations the electronics and/or sensor are on the inner surface of the aligner (e.g., the cavity into which the teeth sit).

Although the examples shown above indicate that the microneedle(s) are extending from an outer surface of the aligner, in some variations some or all of the microneedles may extend from an inner surface of the aligner and into the gingiva or may sample from the saliva above the gingiva. In particular, the one or more microneedles may be configured to sample from the space between the patient's teeth.

In addition to the biosensors described above, also described herein are sensors configured to determine stress-induced bioelectric potentials on the teeth. Stress-induced bioelectric potentials may regulate alveolar bone remodeling during orthodontic tooth movement. For example, the force, F, applied to the labial surface of the lower incisor that displaces the tooth in its socket, deforming the alveolar bone convexly towards the root at the leading edge, may produce concavity towards the root at the trailing edge. Concave bone surfaces characterized by osteoblastic activity are electronegative; convex bone surfaces characterized by osteoclastic activity are electropositive or electrically neutral. Measuring the electrical charge on the teeth surface, may be used to determine the tooth movement rate and direction. Such data can be used to conduct a closed-loop orthodontic treatment. For example, any of the methods an apparatuses described herein may measure or detect the electrical charges from the surface of different regions of a subject's teeth. An apparatus may include a plurality of electrodes within the concavity of an aligner, or a plurality of electrical contacts for contacting electrodes attached to the teeth, e.g., attached to one or both of the buccal and lingual sides of any of the teeth that are being moved by the orthodontic appliance. The apparatus may include the electrical system that is configured to receive these surface charge readings and may store, transmit (e.g., wireless) or analyze these signals, e.g., in the electrical system or remotely, to determine and/or evaluate forces on the teeth and tooth movement.

Also described herein are systems and apparatuses for determining one or more indicator of the patient's heath. For example, any of these methods and apparatuses may include a sensor configured as a physiological sensor to detect one or more subject physiological state. For example, any of the apparatuses or methods described herein may measure (e.g., using a physiological sensor) one or more of: electrocardiogram (ECG), bio-impedance, blood oxygenation, galvanic skin response, heart rate, body temperature, respiration (including respiration rate), or the like. For example, any of these apparatuses may include an ECG sensor (e.g., one-point ECG electrode), a thermistor, a bio-impedance sensor, a photoplethysmogram sensor, a galvanic skin response sensor, etc., including electronics to support such sensor(s). These sensors can be utilized by themselves or with any other sensor, including one or more of the biosensors described herein. As with any of the biosensors and sensors described herein, these sensors may be used to detect or determine compliance (e.g., use of the aligners) while they generate health information of the patient. For instance, a photoplethysmogram (PPG) sensor may measure blood-volume changes in the blood tissue. A plethysmogram is volumetric measurement of an organ. This technique is non-invasive and may be obtained by illuminating light into the body and measuring the change in light absorption. In the current invention, this technique may be applied within the intraoral cavity. A plethysmography sensor can be incorporated in an orthodontic appliance (e.g., aligner) to determine the blood volume change in a cheek or within an extended gingiva segment near or under the appliance to detect blood volume change in gingiva.

Alternatively or additionally, a galvanic skin response (GSR) sensor may be used to measure conductivity of intraoral tissues. Conductivity may change with both changes in the underlying amount of minerals released onto the outer surface of tissues from glands.

Also described herein are methods and apparatuses for detecting and/or analyzing breath. For example any of the apparatuses described herein may be used to detect and/or diagnose disease. For instance, lung and breath cancers may be detected via analysis of the breath, e.g., by identifying particular breath volatile organic compounds (B VOCs) that differ between patients with non-small cell lung cancer (NSCLC) and subjects without the disease. Other sensors that detect cancer at early stages via, for instance, measuring chemical components of breath during exhale. Exhaled breath contains both volatile and non-volatile organic compounds, which vary between healthy individuals and those with lung cancer.

The apparatuses and methods described herein may also be configured to detect halitosis (bad breath). Halitosis may arise from inside the mouth and/or due to a disorders in the nose, sinuses, throat, lungs, esophagus, or stomach. Bad breath may also be due to an underlying medical condition such as liver failure or ketoacidosis. Halitosis may also arise from an underlying disease such as gum disease, tooth decay, or gastroesophageal reflux disease.

By far the most common causes of halitosis are odor producing biofilm on the back of the tongue, below the gum line, and in the pockets created by gum disease between teeth and the gums. This biofilm results in the production of high levels of foul odors produced mainly due to the breakdown of proteins into individual amino acids, followed by the further breakdown of certain amino acids to produce detectable gases. Volatile sulfur compounds are associated with oral malodor levels, and usually decrease following successful treatment. The intensity of bad breath may differ during the day, due to eating certain foods (such as garlic, onions, meat, fish, and cheese), smoking, and alcohol consumption. The odor may be worse upon awakening and may be transient or persistent (e.g., chronic bad breath).

The apparatuses and methods described herein may be configured to detect one or more compounds or markers for bad breath (e.g., above a target threshold) that may indicate bad breath, and may alert the wearer, track, store, and/or transmit detected levels. Markers that may be detected by the apparatuses described herein may include indole, skatole, polyamines, volatile sulfur compounds (VSCs) such as hydrogen sulfide, methyl mercaptan, allyl methyl sulfide, and dimethyl sulfide. In some variations the apparatus may detect one or more bacterial markers arising due to halitosis-producing bacteria. Bacteria that cause gingivitis and periodontal disease (periodontopathogens) may be gram negative may produce VSC. Methyl mercaptan is known to be a contributing VSC in halitosis that and may be caused by periodontal disease and gingivitis.

These apparatuses may also be used to determine, detect and/or diagnose other dental issued, including gum disease. For example, the level of VSC on breath has been shown to positively correlate with the depth of periodontal pocketing, the number of pockets, and whether the pockets bleed when examined with a dental probe. VSC may themselves contribute to the inflammation and tissue damage that is characteristic of periodontal disease. Markers for halitosis may also suggest or indicate infection (e.g., oral infection), oral ulceration, stress/anxiety, menstrual cycle (e.g., at mid cycle and during menstruation, increased breath VSC has been reported), or the like. Any of the methods and apparatuses described herein may also or alternatively be used to detect or determine (and/or aid in treatment) of any of these indications.

For example, a dental apparatus including a sensor may be configured to detect sulfide (e.g., sulfur emissions) from the patient's breath, saliva and/or GCF. For example, the sensor may be configured to detect hydrogen sulfide. Alternatively or additionally, the apparatus may be configured to detect methyl mercaptan, and dimethyl sulfide. In some variations the sensor may be configured to detect a salivary levels of an enzyme indicating the presence of certain halitosis-related bacteria, such as β-galactosidase.

Any of the apparatuses described herein may include microfluidics (e.g., lab-on-a-chip) components. Microfluidics may be used as part of the biosensor, for example, including channels for acquiring a biological fluid (e.g., saliva and/or GCF), processing the fluid (e.g., combining with one or more reagents and/or detecting an interaction with a biomolecule, etc.). The microneedles may be coupled to any of the microfluidics components.

Also included herein is the use of one or more bio sensors (e.g., integrated with an orthodontic appliance such as an aligner) to detect either a protein or DNA component of an allergen. See, e.g., Alves et al., describing a biosensor system for food allergen detection (e.g., Alves et al. 2015. DOI: 10.1080/10408398.2013.831026). As described herein, biosensors are well-suited to automation and their ability to detect multiple analytes in one test with minimal sample preparation and may be used to conduct in vivo detection and detect the presence of food allergens in close to real-time. For example, surface plasmon resonance (SPR)-based biosensors, typically used to the fast detection of egg-related fining allergens in wines, can be integrated with any of the orthodontic appliances (e.g., aligners) described herein to allow rapid detection the presence of egg white allergens at concentrations between 0.03 and 0.20 μg/mL.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

In general, the methods and apparatuses described herein may be used for monitoring the progress of appliance-based orthodontic treatment and/or compliance. Generally, a monitoring apparatus may include one or more biosensors and/or sensors (e.g., physiological sensors) configured to generate sensor data; this data may be related to repositioning of a patient's teeth using an orthodontic appliance. The biosensor and/or sensor data can be processed and analyzed to determine whether the appliance is successfully repositioning the teeth according to prescribed treatment plan. Advantageously, also described herein are integrated electronic sensing and logging systems capable of generating more reliable and accurate aligner performance data, which may be used by the treating practitioner to track treatment progress and adjust the patient's treatment plan if desired. The monitoring devices of the present disclosure can provide high value sensing data useful for adaptive closed-loop treatment planning and appliance design.

Monitoring performance of an orthodontic appliance for repositioning a patient's teeth is described. The apparatus can comprise an orthodontic appliance comprising one or more teeth-receiving cavities shaped to reposition the patient's teeth from an initial arrangement towards a target arrangement. The device can comprise one or more sensors configured to generate sensor data related to the repositioning of the patient's teeth by the orthodontic appliance. The device can comprise a processor configured to process the biosensor/sensor data in order to evaluate the performance of the orthodontic appliance in effecting the repositioning of the patient's teeth.

The performance of the orthodontic appliance can be measured in a variety of ways. For example, the processor may be configured to evaluate the performance of the orthodontic appliance by using the biosensor and/or sensor data to determine one or more of: an amount of force or pressure applied to the patient's teeth, a distribution of force or pressure on the patient's teeth, an amount of movement of the patient's teeth, or a movement rate of the patient's teeth, and/or the phase of movement of the patient's teeth (e.g., initial phase, a lag phase, and a post-lag phase, etc.).

The performance of the orthodontic appliance can determine one or more of: determining if movement is happening, what phase of tooth movement the patient is experiencing, and/or the rate of tooth movement. This information may be processed on the orthodontic appliance itself or off of the appliance (in a remote processor, etc.) and communicated to the dental professional and/or patient. This information may be used to adjust the treatment plan, including instruction removal of an orthodontic appliance (e.g., a removable orthodontic appliance/device) ahead of a scheduled removal, leaving the orthodontic appliance on longer than a scheduled removal date, or maintaining the scheduled removal/replacement date. In some variations the information (e.g., the information derived by monitoring the level of one or more biomarkers using the biosensors) may be used to modify the treatment plan by triggering replacement of one or more devices (aligners) within a planned sequence of removable orthodontic appliances.

In addition to the biosensors described herein, any of these methods and apparatuses may include a force or pressure sensor configured to measure force or pressure applied to one or more teeth by the orthodontic appliance. A force or pressure sensor can comprise a force- or pressure-sensitive film, a resistive film, a capacitive film, or a piezoelectric tactile sensor. The processor can be configured to evaluate the performance of the orthodontic appliance by determining whether an amount of force or pressure applied to the patient's teeth by the orthodontic appliance is within a targeted range. Any of these sensors may be used in combination with one or more biosensor, e.g., to confirm or estimate movement of the teeth.

A movement sensor may be included and configured to measure movement of one or more teeth. A movement sensor can comprise an electromagnetic field generator configured to generate an electromagnetic field. A movement sensor can be configured to measure the movement of the one or more teeth by measuring changes to the electromagnetic field. For instance, a movement sensor can comprise one or more electromagnetic targets arranged to move in response to the movement of the one or more teeth, such that movement of the one or more electromagnetic targets produces changes to the electromagnetic field.

Any of the apparatuses described herein may include a plurality of different biosensor and/or sensors operably coupled to different portions of the orthodontic appliance. The same or different microneedles may be coupled with one or more different biosensors. Any or all of these biosensors/sensors and microneedles can be integrated with the orthodontic appliance, coupled to a tooth, or a combination thereof. As discussed above, a processor may be integrated with the orthodontic appliance or coupled to a tooth. Alternatively, a processor can be located external to the patient's intraoral cavity. Any of these apparatuses my further comprises a communication module configured to transmit one or more of the sensor data or the processed sensor data to a remote device.

A method for monitoring performance of an orthodontic appliance for repositioning a patient's teeth may include receiving biosensor and/or sensor data related to the repositioning of the patient's teeth by the orthodontic appliance from one or more biosensors and/or sensors. The orthodontic appliance can comprise one or more teeth-receiving cavities shaped to reposition the patient's teeth from an initial arrangement towards a target arrangement. The biosensor data can be processed in order to evaluate the performance of the orthodontic appliance in effecting the repositioning of the patient's teeth.

Performance of the orthodontic appliance may be evaluated by using the biosensor data to determine one or more of: the state of a biomarker associated with tooth movement and/or remodeling, an amount of force or pressure applied to the patient's teeth, a distribution of force or pressure on the patient's teeth, an amount of movement of the patient's teeth, or a movement rate of the patient's teeth.

The apparatuses and methods described herein may include transmitting (e.g., wirelessly transmitting) one or more of the sensor and/or biosensor data or the processed sensor data to a remote device.

As mentioned above, the methods and apparatuses described herein can be used in combination with various types of orthodontic appliances. For example, appliances may have teeth-receiving cavities that receive and/or reposition teeth, e.g., via application of force due to appliance resiliency. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. Other orthodontic appliances may include the biosensors and microneedles described herein, including, e.g., palatal expanders. The methods and apparatuses described herein may be used with any appliance that receives teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements on teeth with corresponding receptacles or apertures in the appliance so that the appliance can apply a selected force on the tooth.

As used herein, a dental appliance may include an aligner, such as those utilized in the Invisalign® System, which are described in numerous patents and patent applications assigned to Align Technology, Inc., including, for example, in U.S. Pat. Nos. 6,450,807, and 5,975,893, as well as on the company's website, which is accessible on the World Wide Web (see, e.g., the url "invisalign.com"). In this specification, the use of the terms "orthodontic aligner", "aligner", or "dental aligner" may be synonymous with the use of the terms "appliance" and "dental appliance" in terms of dental applications. For purposes of clarity, embodiments are hereinafter described within the context of the use and application of appliances, and more specifically "dental appliances."

Examples of tooth-mounted attachments suitable for use with orthodontic appliances are also described in patents and patent applications assigned to Align Technology, Inc., including, for example, U.S. Pat. Nos. 6,309,215 and 6,830,450.

The orthodontic appliances described herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Orthodontic appliances, such as the appliance illustrated in FIG. 1A, may impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

The monitoring devices, including any of the microneedles, described herein can be physically integrated into an orthodontic appliance in a variety of ways. In some embodiments, the monitoring device is integrated into the appliance during or after fabrication of the appliance. For example, the monitoring device can be attached to an appliance using adhesives, fasteners, a latching mechanism, or a combination thereof after the appliance has been fabricated. Optionally, the appliance can be formed with complementary features or structures (e.g., recesses, receptacles, guides, apertures, etc.) shaped to receive and accommodate the monitoring device or components thereof.

A monitoring device may be coupled to the appliance as a prefabricated unit during or after fabrication of the appliance, such as by being inserted and sealed into a receptacle in the appliance, attached to an appliance (e.g., by a latching mechanism, adhesive, fastener). Alternatively, the monitoring device can be assembled in situ on the appliance during or after appliance fabrication. For instance, in embodiments where the appliance is manufactured by direct fabrication (e.g., 3D printing), the monitoring device can be printed simultaneously with the appliance, inserted into the appliance during fabrication, or after assembled the appliance has been fabricated. Optionally, some of the monitoring device components may be prefabricated and other components may be assembled in situ. It shall be appreciated that the various fabrication methods described herein can be combined in various ways in order to produce an appliance with integrated monitoring device components.

An orthodontic appliance can be operably coupled to a monitoring device configured to provide data related to tooth repositioning and/or the interaction between the appliance and the patient's teeth (e.g., contact between the appliance and the teeth, the amount of force and/or pressure applied by the appliance to the teeth, distribution of force and/or pressure on the teeth, etc.). Such data can be used to evaluate the performance of the orthodontic appliance for repositioning the patient's teeth. For instance, appliance performance information as described herein can include information regarding whether the force(s), pressure(s), and/or tooth movement(s) produced by an orthodontic appliance correlate with the expected values for the planned orthodontic treatment.

The monitoring devices described herein can be designed for use in the patient's intraoral cavity. For example, the dimensions of a monitoring device may be limited in order to avoid patient discomfort and/or facilitate integration into an orthodontic appliance as discussed below. In some embodiments, a monitoring device has a height or thickness less than or equal to about 1.5 mm, or less than or equal to about 2 mm. In some embodiments, a monitoring device has a length or width less than or equal to about 4 mm, or less than or equal to about 5 mm. The shape of the monitoring device can be varied as desired, e.g., circular, ellipsoidal, triangular, square, rectangular, etc. For instance, in some embodiments, a monitoring device can have a circular shape with a diameter less than or equal to about 5 mm.

A relatively thin and flexible monitoring device can be used to provide a larger surface area while reducing patient discomfort. In some embodiments, the monitoring devices herein are sized to conform to a surface of a tooth crown (e.g., a buccal, lingual, and/or occlusal surface of a tooth crown). For example, a monitoring device having dimensions of about 10 mm by about 5 mm can be used to cover a buccal surface of a molar crown. As another example, a monitoring device having dimensions of about 10 mm by about 20 mm can be used to cover the buccal, occlusal, and lingual surfaces of a tooth crown. A monitoring device can be in contact with a crown of a single tooth, or with crowns of a plurality of teeth, as desired.

The monitoring device dimensions (e.g., volume, weight) can be designed in order to reduce patient discomfort. For instance, the weight of a monitoring device can be selected not to exceed a level that would exert undesirable forces on the underlying teeth. A monitoring device may be used primarily for research and characterization purposes, rather than for patient treatment, and thus may not be subject to size constraints for reducing patient discomfort. For example, in embodiments where the monitoring device is used outside the intraoral cavity (e.g., benchtop testing of aligner performance), the size of the monitoring device can be relatively large compared to devices designed for intraoral use.

As discussed above, FIG. 7A schematically illustrates an example of an apparatus (e.g., a monitoring device 700 portion of an apparatus), that may be used or include an orthodontic appliance (not shown). The monitoring device 700 can be used in combination with any embodiment of the systems and devices described herein, including in combination with any of the microneedles describe herein, and the components of the monitoring device 700 are equally applicable to any other embodiment of the apparatuses described herein. The monitoring device 700 can be implemented as an application-specific integrated circuit (ASIC) including one or more of the following components: a processor 702, a memory 704, one or more biosensors and/or sensors 706, a clock 708, a communication unit 710, an antenna 712, a power management unit 714, or a power source 716. The processor 702 (e.g., a central processing unit (CPU), microprocessor, field programmable gate array (FPGA), logic or state machine circuit, etc.), also referred to herein as a controller, can be configured to perform the various methods described herein. The memory 704 encompasses various types of memory known to those of skill in the art, such as RAM (e.g., SRAM, DRAM), ROM (EPROM, PROM, MROM), or hybrid memory (e.g., flash, NVRAM, EEPROM), and the like. The memory 704 can be used to store instructions executable by the processor 702 to perform the methods provided herein. Additionally, the memory can be used to store biosensor/sensor data obtained by the biosensor(s)/sensors 706, as discussed in greater detail below. Either the biosensor 733 or the electronics subsystem 735 or both may include and/or be coupled with one or more microneedles 727 (in some variations including a bias 728) that may provide sample (e.g., saliva, blood, GCF, etc.) to the sensor(s).

The monitoring device 700 can include any number of biosensors 706 and/or sensor 706', such as one, two, three, four, five, or more biosensors. In some embodiments, the use of multiple biosensors provides redundancy to increase the accuracy and reliability of the resultant data. Some or all of the biosensors 706 can be of the same type. Some or all of the biosensors 706 can be of different types. Examples of biosensor types suitable for use in the monitoring devices described herein are provided below. Examples of additional sensors may include: touch or tactile sensors (e.g., capacitive, resistive), proximity sensors, movement sensors (e.g., electromagnetic field sensors), force sensors (e.g., force-sensitive resistive or capacitive materials), pressure sensors (e.g., pressure-sensitive resistive or capacitive materials), strain gauges (e.g., resistive- or MEMS-based), electrical sensors, or combinations thereof.

A biosensor 706 can be operably coupled to and/or located at any portion of an orthodontic appliance, such as at or near a distal portion, a mesial portion, a buccal portion, a lingual portion, a gingival portion, an occlusal portion, or a combination thereof. A biosensor 706 can be positioned near a tissue of interest when the appliance is worn in the patient's mouth, such as near or adjacent the teeth, gingiva, palate, lips, tongue, cheeks, airway, or a combination thereof. For example, when the appliance is worn, the biosensor(s) 706 can cover a single tooth, or a portion of a single tooth. Alternatively, the biosensor(s) 706 can cover multiple teeth or portions thereof. In embodiments where multiple biosensors 706 are used, some or all of the monitoring devices can be located at different portions of the appliance and/or intraoral cavity. Alternatively, some or all of the biosensors 706 can be located at the same portion of the appliance and/or intraoral cavity.

An analog-to-digital converter (ADC) (not shown) can be used to convert analog biosensor and/or sensor data into digital format, if desired. The processor 702 can process the data obtained by the biosensor(s) 706 in order to determine appliance usage and/or patient compliance, as described herein. The biosensor data and/or processing results can be stored in the memory 704. Optionally, the stored data can be associated with a timestamp generated by the clock 708 (e.g., a real-time clock or counter).

In some embodiments, the monitoring device 700 incudes a communication unit 710 configured to transmit the data stored in the memory (e.g., biosensor data and/or processing results) to a remote device. The communication unit 710 can utilize any suitable communication method, such as wired or wireless communication methods (e.g., RFID, near-field communication, Bluetooth, ZigBee, infrared, etc.). The communication unit 710 can include a transmitter for transmitting data to the remote device and an antenna 712. Optionally, the communication unit 710 includes a receiver for receiving data from the remote device. In some embodiments, the communication channel utilized by the communication unit 710 can also be used to power the device 700, e.g., during data transfer or if the device 700 is used passively.

The remote device can be any computing device or system, such as a mobile device (e.g., smartphone), personal computer, laptop, tablet, wearable device, etc. Optionally, the remote device can be a part of or connected to a cloud computing system ("in the cloud"). The remote device can be associated with the patient, the treating practitioner, medical practitioners, researchers, etc. In some embodiments, the remote device is configured to process and analyze the data from the monitoring device 700, e.g., in order to assess appliance performance, for research purposes, and the like.

The monitoring device 700 can be powered by a power source 716, such as a battery. In some embodiments, the power source 716 is a printed and/or flexible battery, such as a zinc-carbon flexible battery, a zinc-manganese dioxide printed flexible battery, or a solid-state thin film lithium phosphorus oxynitride battery. The use of printed and/or flexible batteries can be advantageous for reducing the overall size of the monitoring device 700 and avoiding patient discomfort. For example, printed batteries can be fabricated in a wide variety of shapes and can be stacked to make three-dimensional structures, e.g., to conform the appliance and/or teeth geometries. Likewise, flexible batteries can be shaped to lie flush with the surfaces of the appliance and/or teeth. Alternatively or in combination, other types of batteries can be used, such as supercapacitors. In some embodiments, the power source 716 can utilize lower power energy harvesting methods (e.g., thermodynamic, electrodynamic, piezoelectric) in order to generate power for the monitoring device 700. Optionally, the power source 716 can be rechargeable, for example, using via inductive or wireless methods. In some embodiments, the patient can recharge the power source 716 when the appliance is not use. For example, the patient can remove the orthodontic appliance when brushing the teeth and place the appliance on an inductive power hub to recharge the power source 716.

Optionally, the apparatus can include a power management unit 714 connected to the power source 716. The power management unit 714 can be configured to control when the apparatus is active (e.g., using power from the power source 716) and when the apparatus inactive (e.g., not using power from the power source 716). In some embodiments, the monitoring device 700 is only active during certain times so as to lower power consumption and reduce the size of the power source 716, thus allowing for a smaller monitoring device 700

The apparatus may also include an activation mechanism (not shown) for controlling when the monitoring device (e.g., control circuitry) 700 is active (e.g., powered on, monitoring appliance usage) and when the monitoring device 700 is dormant (e.g., powered off, not monitoring appliance usage). The activation mechanism may deploy and/or retract the microneedles. The activation mechanism can be provided as a discrete component of the monitoring device 700, or can be implemented by the processor 702, the power management unit 714, or a combination thereof. The activation mechanism can be used to reduce the amount of power used by the monitoring device 700, e.g., by inactivating the device 700 when not in use, which can be beneficial for reducing the size of the power supply 716 and thus the overall device size.

In some embodiments, the monitoring device 700 is dormant before being delivered to the patient (e.g., during storage, shipment, etc.) and is activated only when ready for use. This approach can be beneficial in conserving power expenditure. For example, the components of the monitoring device 700 can be electrically coupled to the power source 716 at assembly, but may be in a dormant state until activated, e.g., by an external device such as a mobile device, personal computer, laptop, tablet, wearable device, power hub etc. The microneedles may be retracted (and in some variations may be housed within a housing). The external device can transmit a signal to the monitoring device 700 that causes the activation mechanism to activate the monitoring device 700, and extension of the microneedle(s). As another example, the activation mechanism can include a switch (e.g., mechanical, electronic, optical, magnetic, etc.), such that the power source 716 is not electrically coupled to the other components of the monitoring device 700 until the switch is triggered. For example, the switch may be a reed switch or other magnetic sensor that is held open by a magnet. The magnet can be removably attached to the monitoring device 700, or may be integrated into the packaging for the device 700 or appliance, for example. When the monitoring device is separated from the magnet (e.g., by removing the magnet or removing the device and appliance from the packaging), the switch closes and connects the power source 716, as illustrate in FIG. 7B. As another example, the monitoring device 700 can include a mechanical switch such as a push button that is manually actuated in order to connect the power source 716. In some embodiments, the activation mechanism includes a latching function that locks the switch upon the first actuation to maintain connectivity with the power source so as to maintain activation of the monitoring device 700. Optionally, the switch for the activation mechanism can be activated by a component in the patient's intraoral cavity (e.g., a magnet coupled to a patient's tooth), such that the monitoring device 700 is active only when the appliance is worn by the patient, and is inactive when the appliance is removed from the patient's mouth. Alternatively or in combination, the switch can be activated by other types of signals, such as an optical signal.

FIG. 7B illustrates a monitoring device 700 with an activation mechanism. The monitoring device 700, as with all other monitoring devices described herein, can be similar to the monitoring device 700, and can include some or all of the components described herein with respect to the monitoring device 700. The device 700 is coupled to an orthodontic appliance 702 (e.g., via an encapsulating material 404). The device 400 can include an activation mechanism 703 including a magnetic switch. Prior to use, the device 700 can be removably coupled to a magnet 706 (e.g., using tape 708), and the magnet 706 can hold the magnetic switch in an open position such that the device 700 is inactive. When the appliance 702 is ready for use, the user can remove the magnet 706, thus closing the magnetic switch and connecting the components of the monitoring device 700 to a power source.

The orthodontic appliances and monitoring devices can be configured in many different ways. In some embodiments, an orthodontic appliance may be operably coupled to a single monitoring device. Alternatively, the orthodontic appliance can be operably coupled to a plurality of monitoring devices, such as at least two, three, four, five, or more monitoring devices. Some or all of the monitoring devices may be of the same type (e.g., collect the same type of data). Alternatively, some or all of the monitoring devices may be of different types (e.g., collect different types of data). Any of the embodiments of monitoring devices described herein can be used in combination with other embodiments in a single orthodontic appliance.

A monitoring device, including one or more microneedles, can be located at any portion of the appliance, such as at or near a distal portion, a mesial portion, a buccal portion, a lingual portion, a gingival portion, an occlusal portion, or a combination thereof. The monitoring device can be positioned near a tissue of interest when the appliance is worn in the patient's mouth, such as near or adjacent the teeth, gingiva, palate, lips, tongue, cheeks, airway, or a combination thereof. For example, when the appliance is worn, the monitoring device can cover a single tooth, or a portion of a single tooth. Alternatively, the monitoring device can cover multiple teeth or portions thereof. In embodiments where multiple monitoring devices are used, some or all of the monitoring devices can be located at different portions of the appliance. Alternatively, some or all of the monitoring devices can be located at the same portion of the appliance.

A monitoring device can be operably coupled to the orthodontic appliance in a variety of ways. For example, the monitoring device can be physically integrated with the orthodontic appliance by coupling the monitoring device to a portion of the appliance (e.g., using adhesives, fasteners, latching, laminating, molding, etc.). The coupling may be a releasable coupling allowing for removal of the monitoring device from the appliance, or may be a permanent coupling in which the monitoring device is permanently affixed to the appliance. Alternatively or in combination, the monitoring device can be physically integrated with the orthodontic appliance by encapsulating, embedding, printing, or otherwise forming the monitoring device with the appliance. In some embodiments, the appliance includes a shell shaped to receive the patient's teeth, and the monitoring device is physically integrated with the shell. The monitoring device can be located on an inner surface of the shell (e.g., the surface adjacent to the received teeth), an outer surface of the shell (e.g., the surface away from the received teeth), or within a wall of the shell. Optionally, as discussed further herein, the shell can include a receptacle shaped to receive the monitoring device. Exemplary methods for fabricating an appliance with a physically integrated monitoring device (e.g., by incorporating some or all of the components of the monitoring device during direct fabrication of the appliance) are described in further detail herein.

FIG. 9 illustrate an example of an apparatus including an orthodontic appliance 900 having an integrated monitoring device (control circuitry) 902 and biosensor and one or more microneedles 917. In this example, the appliance 900 includes a shell 904 having one or more (e.g., a plurality of) teeth-receiving cavities, and the monitoring device 902 is coupled to an outer, buccal surface of the shell 904 adjacent a tooth receiving cavity 906. In the depicted embodiment, the monitoring device 902 is coupled to a tooth receiving cavity 906 for a molar. It shall be appreciated that in alternative embodiments, the monitoring device 902 can be coupled to other portions of the shell 904, such as an inner surface, a lingual surface, an occlusal surface, one or more tooth receiving cavities for other types of teeth (e.g., incisor, canine, premolar), etc. The monitoring device 902 can be shaped to conform to the geometry of the corresponding appliance portion (e.g., the wall of the cavity 906) so as to provide a lower surface profile and reduce patient discomfort. In some embodiments, the appliance 900 includes a receptacle 908 formed on the outer surface of the shell 904 and the monitoring device 902 is positioned within the receptacle. Exemplary methods for forming an appliance with a receptacle 908 and integrated monitoring device 902 are described in detail below.

The monitoring device 902 can include a biosensor 910 and/or sensor, one or more microneedles 917, a power source 912 (e.g., a battery), and/or a communication unit 914 (e.g., a wireless antenna). The arrangement of the components of the monitoring device 902 can be varied as desired. In some embodiments, the biosensor is located adjacent to the tooth receiving cavity. A gap can be formed in the shell adjacent to the biosensor/sensor so as to permit direct access to the received tooth. The communication unit (or a component thereof, such as an antenna) can be located adjacent to or on the outer surface of the receptacle so as to facilitate data transmission.

A monitoring device can include a single biosensor, or a plurality of biosensors and/or other sensors can be positioned at any location in the appliance, such on an inner surface, an outer surface, a buccal surface, a lingual surface, an occlusal surface, a mesial portion, a distal portion, a gingival portion, or a combination thereof. In embodiments where the orthodontic appliance includes a shell with a teeth-receiving cavity, the biosensors/sensors can be positioned on the inner surfaces of the teeth-receiving cavities. Optionally, at least some biosensors can be located on an outer surface of the appliance, such as an occlusal surface in order to detect contact between the upper and lower teeth The biosensors can be positioned to be near certain teeth when the appliance is worn, e.g., near teeth to be repositioned and/or at locations where the appliance is expected to exert force on the teeth. For example, tactile sensors can be located at or near the buccal, lingual, and/or occlusal surfaces of a tooth to be repositioned so as to provide a map of contact points over the tooth crown. In some embodiments, the monitoring device is configured to obtain data from buccal, lingual, and occlusal sensors in a predetermined order and at a desired frequency in order to provide a contact map over the buccal, lingual, and occlusal surfaces. Alternatively or in combination, if the appliance is shaped to engage an attachment device mounted on a tooth, a tactile sensor can be located at or near the location of engagement between the appliance and the attachment device.

Alternatively or in combination, any of the apparatuses described herein can include one or more conductivity sensors configured to measure the conductivity of fluids (e.g., saliva) in the surrounding environment. In some embodiments, bone remodeling during orthodontic tooth movement causes changes in saliva content, and these changes can be measured based on the ionic charge of the minerals in the saliva. Examples of minerals that may influence the conductivity of saliva include but are not limited to $NH_4+$, $Ca_2+$, $PO_43"$, $HCO_3-$, and $F"$.

In general, the apparatuses described herein may include miniaturized and integrated electronic components (e.g., battery, antenna, controller, wireless communication circuitry, etc.) as part of an embedded biosensing apparatus. In some variations, the biosensor may include detection of one or more types of biomarker in saliva, including those in Table 1, above. For example, a Potentiostat with a screen-printed electrode and a modified enzyme layer may be used to detect a salivary biomarker (e.g., 14-3-3 protein a (Stratifin), uric acid, etc.). A working electrode (biotransducer) may be chemically modified by crosslinking to an enzyme. An antifouling layer may be included to prevent interference effects and biofouling.

The apparatus may include electrodes for differential C2D (e.g., common to differential) measurements and input channels for A2D (analog to digital) voltage measurements. One or more electrodes may be layered with an enzyme-membrane to achieve different configurations of working electrodes. Additional sensors and/or biosensors may be used, including temperature measurements. For example, one or more sensors can provide proximity data, which can augment biomarker detection.

In any of these apparatuses and methods described herein, compliance data may be determined from the biosensor/sensor data, and this information may also be used to augment, control, and/or interpret the biosensor information. For example, compliance data may be estimated by determining a working state of the apparatus from proximity data (e.g., power states for "In-mouth" and "out-of-mouth" conditions). Temperature sensing may also be used to augment biomarker data, e.g., by correlating temperature and biomarker data, which may provide more specific physiological monitoring.

As discussed above, examples of biomarkers that may be detected by the apparatuses and methods herein may include salivary biomarkers such as sRANKL, OPG, which may be correlated to different phases of orthodontic tooth movement (e.g., https://www.ncbi.nlm.nih.gov/pubmed/23273364). Other salivary markers include S100-A9, immunoglobulin J chain, Ig alpha-1 chain C region, CRISP-3, which may indicate inflammation and bone resorption (see, e.g., https://www.ncbi.nlm.nih.gov/pmc/articles/PMC3417200/).
Examples of gingival crevicular fluid biomarkers, e.g., inflammatory fluid accessible in in the gingival margin, may include prostaglandin E2 (which may indicate bone resorption), Substance P (neuropeptide) (which may indicate bone resorption), epidermal growth factor (which may indicate bone resorption), transforming growth factor (which may indicate bone remodeling), RankL (which may indicate stimulation of osteoclastic differentiation), Granulocyte macrophage colony stimulation factor (which may indicate bone turnover), α2 microglobulin-enhance of IGF 1, Interleukin 1β, 2, 6, 8 (which may indicate bone remodeling), Myeloperoxidase (and enzyme involved in PMN inflammation). Other gingival crevicular fluid biomarkers may include glycosaminoglycans (GAGs or mucopolysaccharides), and may indicate paradental remodeling, such as hyaluronic acid (a type of GAG or mucopolysaccharide, indicator of breakdown of gingival tissue), and Chondroitin sulfate (another type of GAG, an indicator of breakdown of alveolar bone and PDL).

Alternatively, as mentioned, a sensor, such as a stretchable sensor, may be bonded directly to the teeth or other intra oral tissue. This may provide better access to GCF or saliva for the biosensor/sensor. Instead of an embedded biosensor on the aligner, the biosensor may be directly bonded to the gingival margin to monitor GCF for certain biomarkers.

Figure 10:
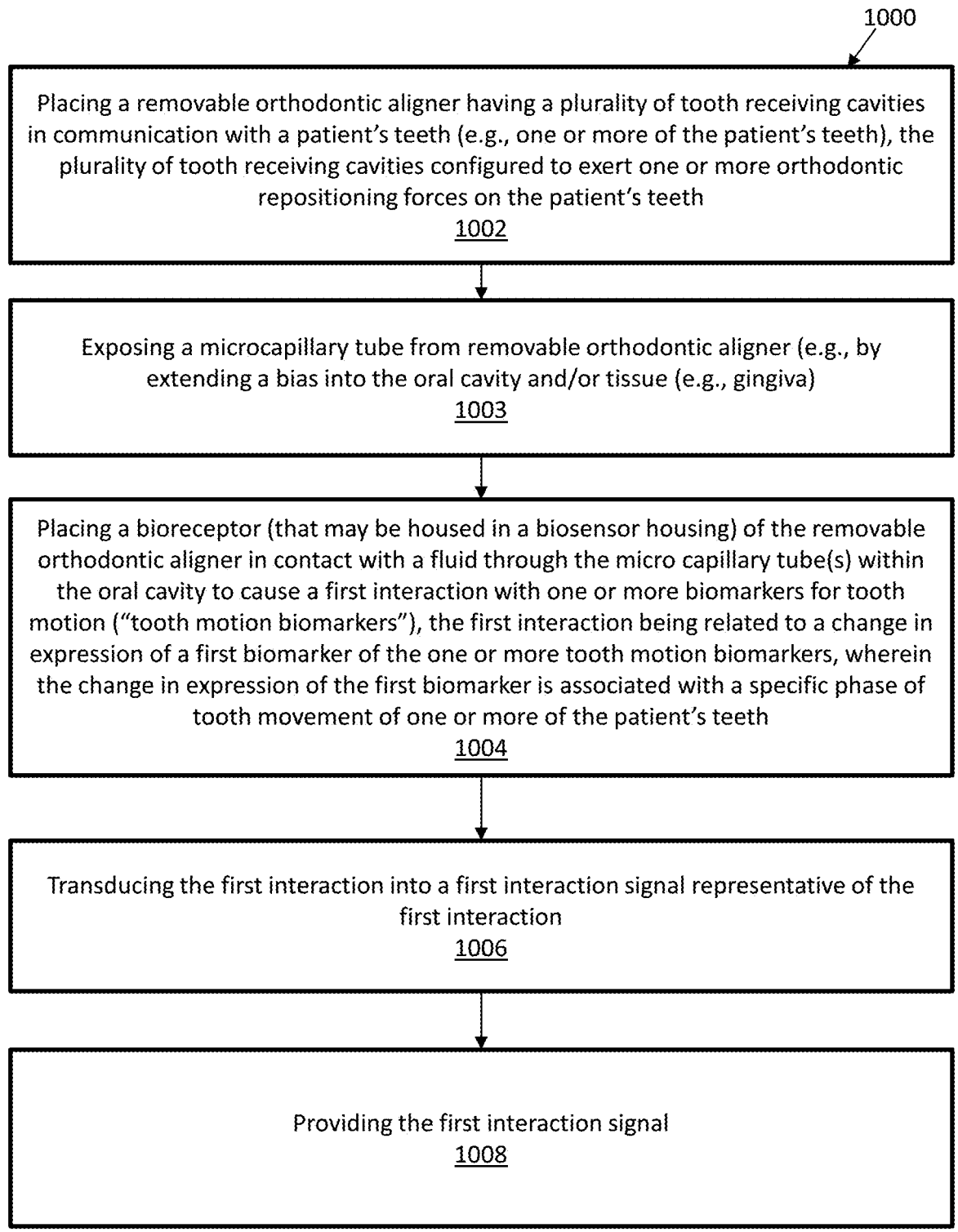
FIG. 10 illustrates an example of a method of operating a removable orthodontic device (e.g., appliance) including a biosensor.
Figure 7A:
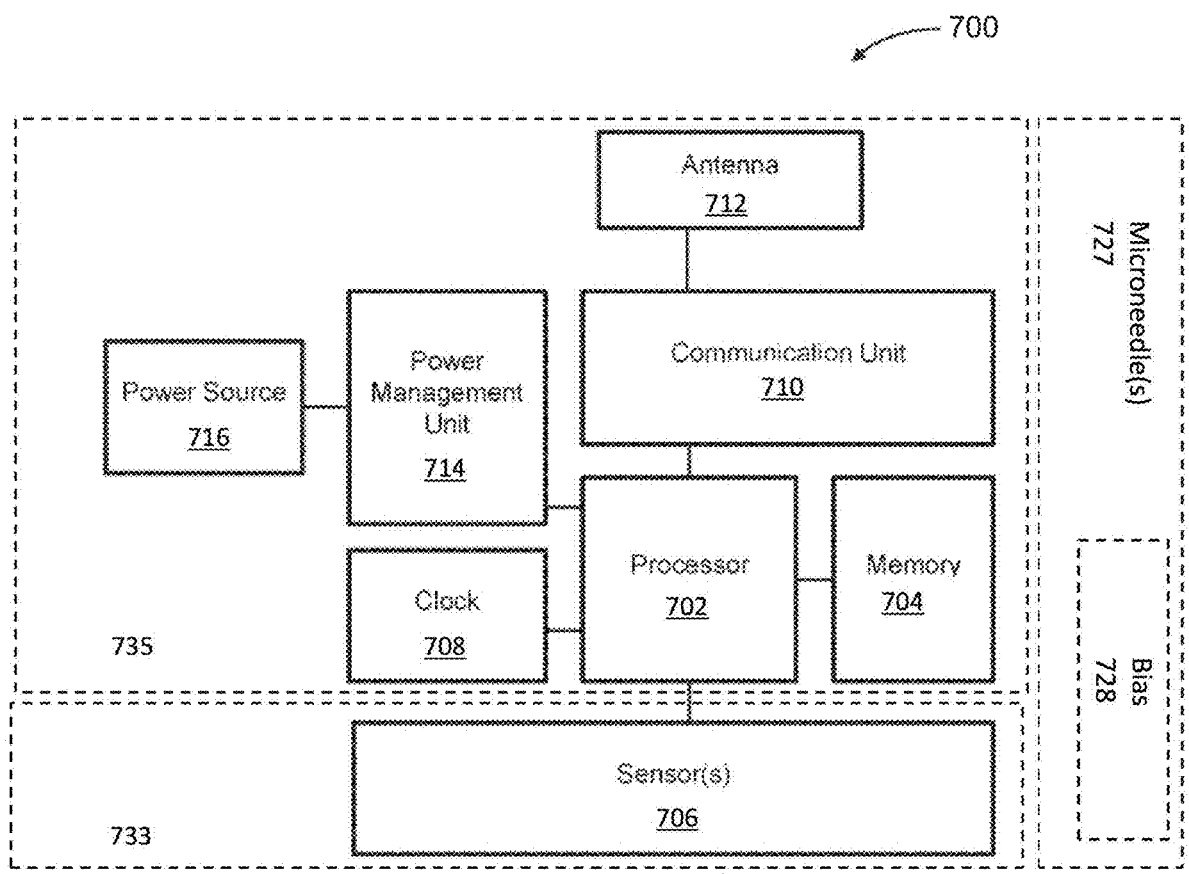
Figure 7B:
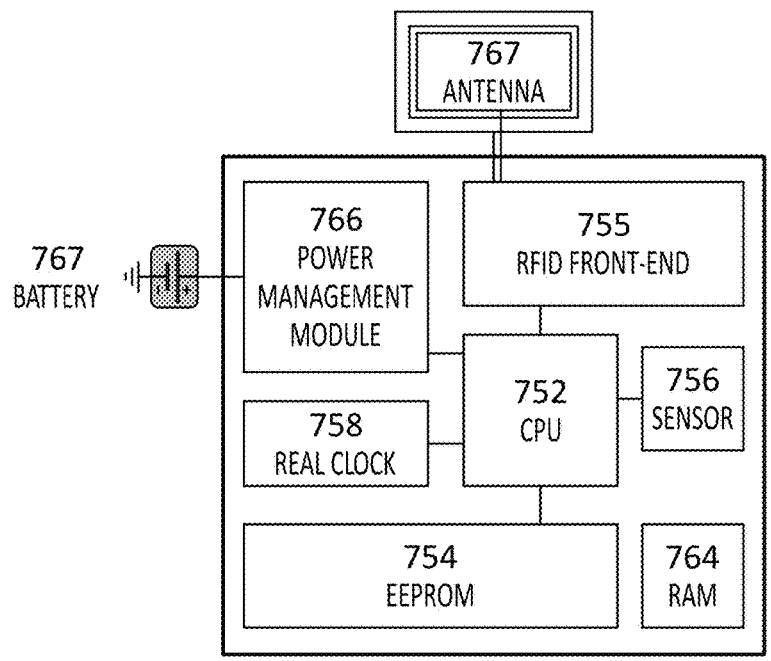
Figure 8A:
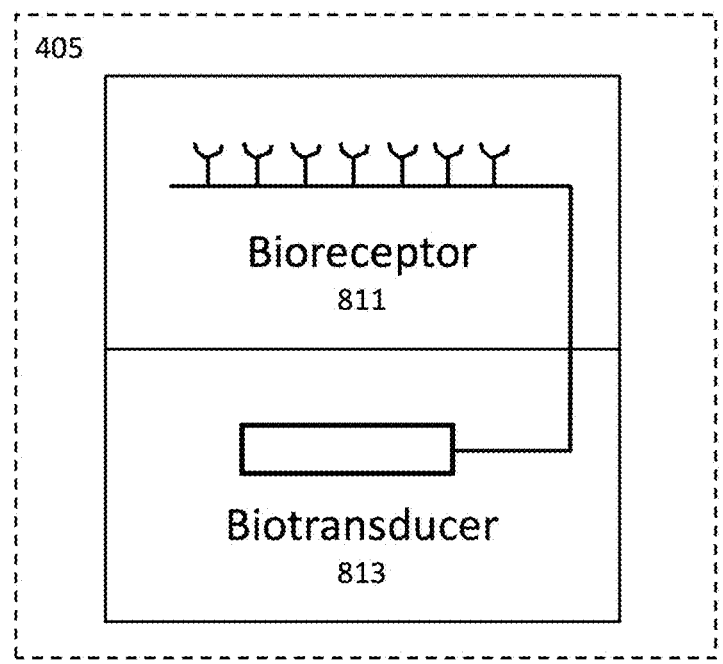
Figure 8B:
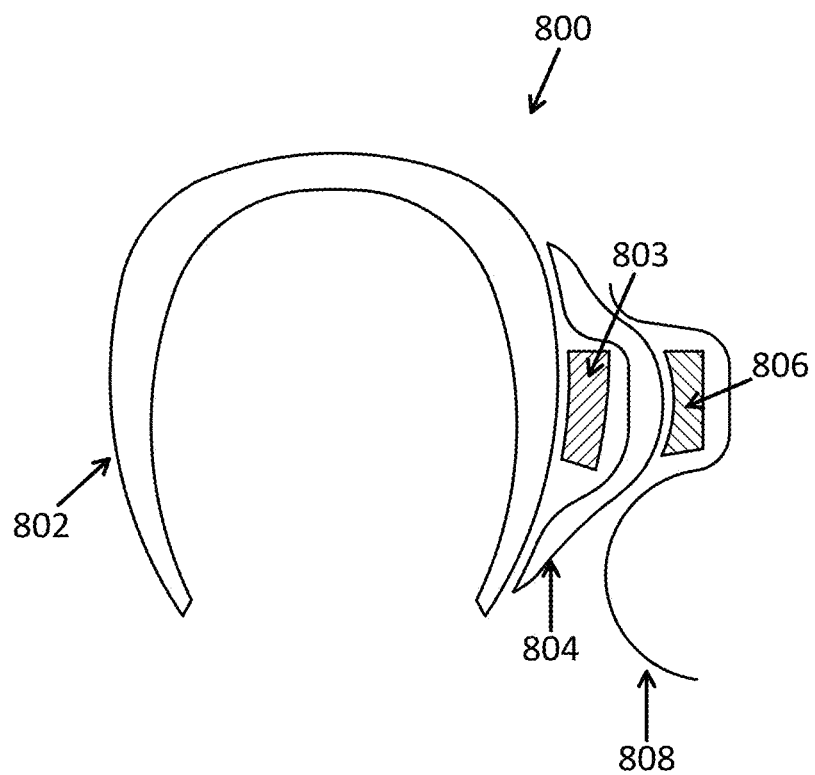
Figure 8C:
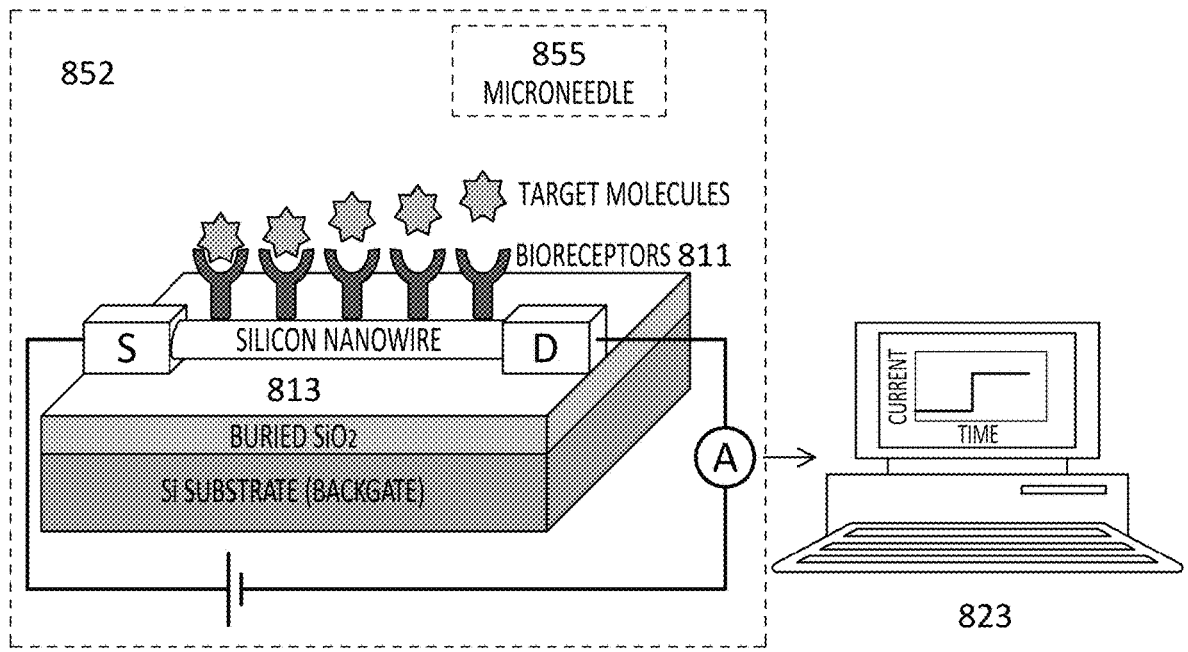
Figure 9:
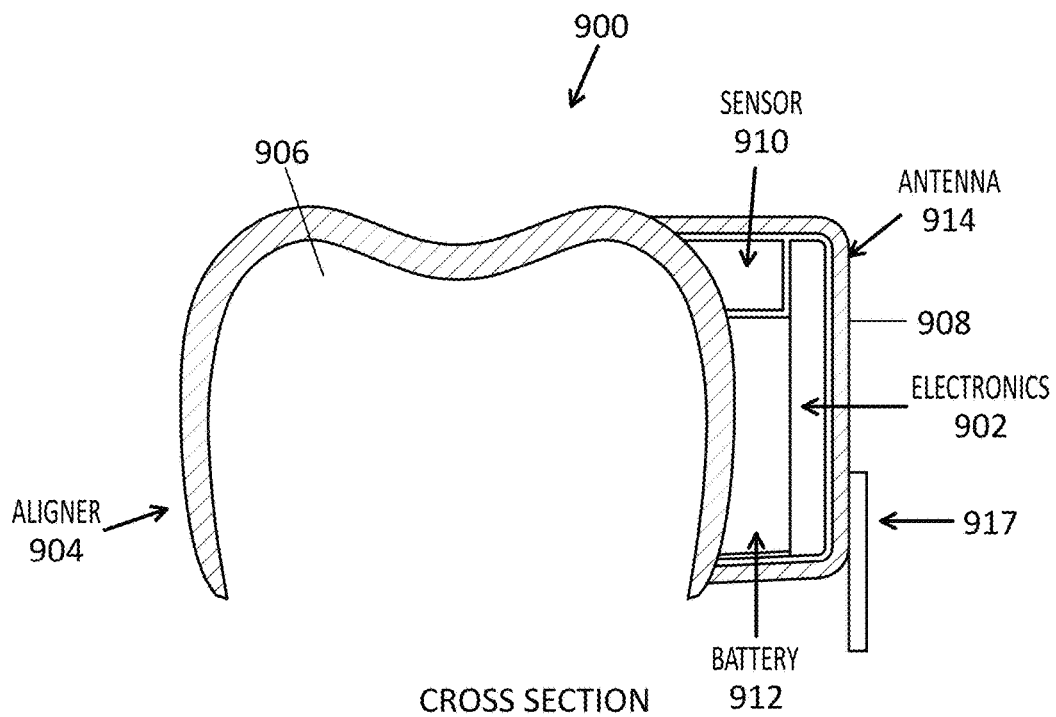

As mentioned above, any of the biosensor systems and apparatuses (e.g., removable orthodontic devices) described herein may be used to monitor one or more biomarkers from a patient. For example, FIG. 10 schematically illustrates one example of a method of monitoring a biomarker from a patient using a removable orthodontic device, such as an aligner, that includes one or more microneedles for detecting a biomarker. As mentioned above, as an initial step (not shown) a removable orthodontic device that does not apply substantial force to move the teeth but that includes a biosensor system may be first worn, and a baseline for the one or more biomarkers collected. In FIG. 10, a removable orthodontic device (e.g., aligner) having a biosensor may be worn by the patient. For example, the removable orthodontic device may have a plurality of tooth receiving cavities that may be placed in communication with a patient's teeth (e.g., one or more of the patient's teeth). The plurality of tooth receiving cavities may be configured to exert one or more orthodontic repositioning forces on the patient's teeth 1002.

While the aligner is worn, the bioreceptor (that may be housed in a biosensor housing) of the removable orthodontic aligner may be placed in contact with a fluid (e.g., saliva, GCF, blood) within the oral cavity, e.g., through the microneedle(s) 1003, as described above, which may cause a first interaction with one or more biomarkers for tooth motion ("tooth motion biomarkers"). The first interaction may be related to a change in expression of a first biomarker of the one or more tooth motion biomarkers, wherein the change in expression of the first biomarker is associated with a specific phase of tooth movement of one or more of the patient's teeth 1004. For example, the level of the biomarker compared to a baseline may be indicative of the phase of tooth movement (e.g., initial phase, lag phase, etc.). A threshold or range of sensed values may be used to monitor an effect of the removable orthodontic device on the teeth. For example, the first interaction may be transduced into a first interaction signal representative of the first interaction 1006, and this first interaction signal may be provided by the device 1008. For example it may be output (transmitted, displayed, stored, etc.).

As mentioned above, any of the biosensors described herein may include one or more microfluidics systems for capture, storage and analysis of intra-oral fluids, including chemical analysis. For example, any of these microfluidic systems may include hard or flexible/stretchable (such as silicone) materials with or without integrated electronics (including wireless communication electronics), and may be formed integrally with the apparatus (e.g., aligner) and/or be intimately and robustly bond to the surface of apparatus. The one or more microneedles described herein may be fluidically linked to the microfluidics system(s).

In some variations, the microfluidic system may include a network of reservoirs for embedded chemical agents that may respond in colorimetric fashion to biomarkers. The reservoirs may be connected by microfluidics channels. In some variations the microfluidics channels may be configured for active and/or passive metering, so that a fluid from within the patient's oral cavity (e.g., saliva and/or GCF) may be drawn into the microfluidics channel (e.g., from the microneedle(s) as described herein) and passed into a sample chamber. The sample chamber may include, for example a colorometric indicator or other chemical agent that responds to one or more biomarkers in the fluid in a colorimetric manner. Alternatively, in some variations, the sample is processed in a microfluidics channel for later read-out (e.g., when removing the device from the mouth, and placing it into a separate storage and/or readout chamber.

In any of these variations, apparatus may include microfluidic channels that are configured to allow access to various sample and/or detection regions on the apparatus at various times. For example, the microfluidics device integrated into or on an aligner may be configured to provide timing via chrono-sampling of a fluid. For example, a microfluidic system can be designed to enable sampling with chronological order and controlled timing. In some variations, the timing of fluid within the microchannel may be timed actively, e.g., by the opening of a channel via release of a valve (e.g., an electromechanical valve, an electromagnetic value, a pressure valve, etc.). Examples of valves controlling fluid in a microfluidic network include piezoelectric, electrokinetics and chemical approaches. Capillary bursting valves (CBVs) are another variation of a valve for a microfluidics channel. CBVs block flows at pressures lower than their characteristic bursting pressures (BPs). When liquid in a single connected channel encounters two separate CBVs with different BPs, at sufficient pressures, the flow will proceed first through the valve with lower BP. In this way, locating two CBVs with different BPs near the intersection between two channels allows control of the direction of flow. The Young-Laplace equation gives the BP in a rectangular channel:

$$BP = -2\sigma\left[\frac{\cos\theta_1^*}{b} + \frac{\cos\theta_A}{h}\right] \quad [1]$$

where σ is the surface tension of liquid, OA is the contact angle of the channel, $\theta_1^*$ is the $\min[\theta_A+\beta; 180°]$, β is the diverging angle of the channel, b and h are the width and the height of the diverging section, respectively. For hydrophobic materials at high diverging angles, the BP increases with decreasing b and h.

Thus, by adjusting the angles and dimensions, the bursting pressure may be adjusted and in the context of a microfluidics channel, series of CBVs may be used to set up a sequence of timed regions that open as the fluid within the channel reaches the selected BP. For example, the diverging angles may be between 13° and 90°, or 13° and 120°. One of skill in the art would therefore be able to select the microfluidic channel lengths and BP configurations to arrange a series of microfluidics channels and chambers, which are valved by one or more control valves, including CBVs that open at predetermined time ranges to allow sampling over time.

In some variations the microfluidic channel may be opened by dissolving a material blocking the channel. The rate of dissolution may be calibrate to open the channel after a predetermined time period (e.g., minutes, hours, days, etc.). In some variations the dissolving material may include one or more reagents for use in detecting and/or storing the fluid in the microfluidics apparatus. For example, a blocking material may include a labeling material (e.g., such as an antibody, enzyme, substrate, etc.) for detection within a chamber blocked by the blocking material.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intraoral system, comprising:
    an aligner shaped to receive a patient's teeth and to resiliently reposition the patient's teeth according to a phase of an orthodontic treatment plan prescribed for the patient;
    a soft tissue sensor mounted to the aligner, wherein the soft tissue sensor comprises one or more microneedles each having an inner lumen configured to pass at least one protein biomarker to the soft tissue sensor, the at least one protein biomarker associated with tooth movement, wherein the soft tissue sensor is configured to chemically detect a level of the at least one protein biomarker collected through the one or more microneedles to determine an effectiveness of the aligner for causing tooth movement according to the phase of the orthodontic treatment plan;
    a processor configured to:
        access data associated with the orthodontic treatment plan;
        compare the detected level of the at least one protein biomarker to an expected level of the at least one protein biomarker, wherein the expected level is based on an expected change in expression of the at least one protein biomarker indicative of tooth movement according to the phase of the orthodontic treatment plan; and
        determine, based on the comparison, that the aligner is to be replaced with another aligner in a planned sequence of aligners;
    a bias coupled to the soft tissue sensor, wherein the bias is configured to apply a continuous force on the soft tissue sensor to hold the one or more microneedles against the patient's soft tissue; and
    a control operationally coupled to the bias, wherein when the aligner is worn on the patient's teeth, activation of the control causes the bias to apply a biasing force on the soft tissue sensor to move the one or more microneedles from a retracted position to an extended position to penetrate the patient's soft tissue adjacent to the patient's teeth.

2. The system of claim 1, wherein the soft tissue sensor is removably mounted to the aligner.

3. The system of claim 1, wherein the soft tissue sensor is configured so as to not interfere with the patient's bite when worn.

4. The system of claim 1, wherein the soft tissue sensor is formed of a translucent or transparent material.

5. The system of claim 1, wherein the bias comprises a spring.

6. The system of claim 1, further comprising one or more attachment sites on the aligner configured to couple with one or more temporary anchorage devices.

7. The system of claim 1, wherein the aligner is configured to screw onto a prosthetic tooth.

8. The system of claim 1, wherein the soft tissue sensor is further configured to detect one or more of: glucose, an inflammatory marker, or a bacterial marker.

9. The system of claim 1, wherein the soft tissue sensor is configured to generate sensor data related to repositioning of the patient's teeth.

10. The system of claim 1, wherein the one or more microneedles are configured to extend between the patient's teeth and collect gingival crevicular fluid.

11. The system of claim 1, wherein the soft tissue sensor is configured to sense a property of saliva, interstitial fluid, lymph, or blood associated with the patient's gingiva.

12. The system of claim 1, wherein the soft tissue sensor includes a bio-receptor configured to interact with the protein biomarker and trigger a signal transduction event.

13. The system of claim 1, wherein the control is coupled to the aligner.

14. The system of claim 1, wherein the soft tissue sensor is detachably mounted to the aligner.

15. The system of claim 1, wherein the control is user activated.

16. The system of claim 1, wherein the soft tissue sensor is configured to detect a concentration of the at least one protein biomarker, wherein the concentration of the at least one protein biomarker is associated with a velocity of tooth movement.

17. The system of claim 1, wherein the soft tissue sensor is configured to convert chemical detection by the soft tissue sensor of the at least one protein biomarker to an electrical output, wherein the soft tissue sensor is further configured to send the electrical output to a detector.

18. The system of claim 17, wherein the soft tissue sensor is further configured to send the electrical output with a timestamp.

19. The system of claim 1, wherein the control is configured to be remotely activated.

20. The system of claim 1, wherein the soft tissue sensor is configured to continuously monitor the level of the at least one protein biomarker.

21. The system of claim 1, wherein the processor is further configured to base the determination on a prior baseline reading.

22. The system of claim 21, wherein the processor is further configured to determine a current phase of treatment based on comparing the detected level of the at least one protein biomarker to the prior baseline reading.

23. The system of claim 1, wherein the soft tissue sensor includes a chemical, immunohistochemical, enzymatic, optical, infrared and/or florescence sensor.

24. A method of detecting a protein biomarker from a patient's soft tissue, the method comprising:
placing an aligner onto the patient's teeth, the aligner comprising a plurality of teeth receiving cavities configured to receive and resiliently reposition the patient's teeth according to a phase of an orthodontic treatment plan prescribed for the patient;
activating a control to bias a soft tissue sensor mounted to the aligner against the patient's soft tissue, wherein the soft tissue sensor comprises one or more microneedles projecting from the aligner, wherein activating the control applies a biasing force on the soft tissue sensor to move the one or more microneedles from a retracted position to an extended position and to penetrate the patient's soft tissue adjacent to the patient's teeth, the one or more microneedles arranged to pass the protein biomarker from the patient's soft tissue to the soft tissue sensor, wherein the protein biomarker is associated with tooth movement;
holding the one or more microneedles against the patient's soft tissue by applying a continuous force on the soft tissue sensor using a bias coupled to the soft tissue sensor;
chemically sensing the protein biomarker collected through the one or more microneedles using the soft tissue sensor; and
detecting a level of the protein biomarker to determine an effectiveness of the aligner for causing tooth movement according to the phase of the orthodontic treatment plan;
wherein a processor of the soft tissue sensor:
accesses data associated with the orthodontic treatment plan;
compares the detected level of the protein biomarker to an expected level of the protein biomarker, wherein the expected level is based on an expected change in expression of the protein biomarker indicative of tooth movement according to the phase of the orthodontic treatment plan; and
determines, based on the comparison, that the aligner is to be replaced with another aligner in a planned sequence of aligners.

25. The method of claim 24, wherein the continuous force is applied from a spring.

26. The method of claim 24, further comprising detecting one or more of: glucose, an inflammatory marker, or a bacterial marker.

27. The method of claim 24, further comprising causing the one or more microneedles to move from the extended position to the retracted position.

28. The method of claim 27, wherein deactivating the control causes the one or more microneedles to move from the extended position to the retracted position.

29. The method of claim 24, further comprising tracking the level of the protein biomarker over a course of treatment by the aligner.

30. The method of claim 24, wherein the aligner is a first aligner of a series of aligners for implementing the orthodontic treatment plan, the method further comprising placing a second aligner of the series of aligners onto the patient's teeth and chemically sensing the protein biomarker using a second soft tissue sensor of the second aligner to confirm movement of the patient's teeth caused by forces applied to the patient's teeth by the second aligner.

31. The method of claim 24, further comprising continuously monitoring the level of the protein biomarker.

32. An intraoral system, comprising:
an aligner shaped to receive a patient's teeth and to resiliently reposition the patient's teeth according to a phase of an orthodontic treatment plan prescribed for the patient;
a soft tissue sensor detachably mounted to the aligner, wherein the soft tissue sensor comprises one or more microneedles configured to pass at least one protein biomarker from the patient's soft tissue to the soft tissue sensor, wherein the soft tissue sensor is configured to chemically detect the at least one protein biomarker associated with tooth movement collected through the one or more microneedles, wherein the soft tissue sensor is configured to detect a level of the at least one protein biomarker to determine an effectiveness of the aligner for causing tooth movement according to the phase of the orthodontic treatment plan;
a processor configured to:
access data associated with the orthodontic treatment plan;
compare the detected level of the at least one protein biomarker to an expected level of the at least one protein biomarker, wherein the expected level is based on an expected change in expression of the at least one protein biomarker indicative of tooth movement according to the phase of the orthodontic treatment plan; and
determine, based on the comparison, that the aligner is to be replaced with another aligner in a planned sequence of aligners; and
a control coupled to soft tissue sensor, wherein when the aligner is worn on the patient's teeth, activation of the control causes a bias to move the one or more microneedles from a retracted position to an extended position and to penetrate the patient's soft tissue adjacent to the patient's teeth, wherein the bias is configured to continuously apply a force on the soft tissue sensor to hold the one or more microneedles against the patient's soft tissue.

33. The system of claim 32, wherein the soft tissue sensor is configured to monitor the effectiveness of the aligner based on whether the level of the at least one protein biomarker achieves a threshold value.

34. The system of claim 32, wherein the processor is further configured to base the determination based on a prior baseline reading.

35. The system of claim 32, wherein the soft tissue sensor is configured to detect multiple different protein biomarkers.

36. The system of claim 32, wherein the soft tissue sensor is further configured to detect one or more of: glucose, an inflammatory marker, or a bacterial marker.

* * * * *